(12) United States Patent
Bebbington et al.

(10) Patent No.: US 8,697,698 B2
(45) Date of Patent: *Apr. 15, 2014

(54) PYRAZOLE COMPOUNDS USEFUL AS PROTEIN KINASE INHIBITORS

(71) Applicant: Vertex Pharmaceuticals Incorporated, Boston, MA (US)

(72) Inventors: David Bebbington, Newbury (GB); Jean-Damien Charrier, Wantage (GB); Julian Golec, Faringdon (GB); Francoise Pierard, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/631,488

(22) Filed: Sep. 28, 2012

(65) Prior Publication Data

US 2013/0096128 A1   Apr. 18, 2013

Related U.S. Application Data

(60) Continuation of application No. 12/109,598, filed on Apr. 25, 2008, now Pat. No. 8,304,414, which is a continuation of application No. 10/775,699, filed on Feb. 10, 2004, now Pat. No. 7,427,681, which is a division of application No. 10/034,019, filed on Dec. 20, 2001, now Pat. No. 6,727,251.

(60) Provisional application No. 60/286,949, filed on Apr. 27, 2001, provisional application No. 60/257,887, filed on Dec. 21, 2000.

(51) Int. Cl.

| A01N 43/64 | (2006.01) |
|---|---|
| A61K 31/53 | (2006.01) |
| A61K 31/50 | (2006.01) |
| A61K 31/501 | (2006.01) |
| C07D 253/00 | (2006.01) |
| C07D 401/00 | (2006.01) |
| C07D 403/00 | (2006.01) |
| C07D 405/00 | (2006.01) |
| C07D 409/00 | (2006.01) |

(52) U.S. Cl.
USPC ....... 514/242; 514/252.05; 544/182; 544/238

(58) Field of Classification Search
None
See application file for complete search history.

(56) References Cited

U.S. PATENT DOCUMENTS

| 3,133,081 A | 5/1964 | Lafferty et al. |
|---|---|---|
| 3,755,322 A | 8/1973 | Winter et al. |
| 3,935,183 A | 1/1976 | Baron et al. |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,579,983 B1 | 6/2003 | Batchelor et al. |
| 6,589,958 B1 | 7/2003 | Frietze |

(Continued)

FOREIGN PATENT DOCUMENTS

| DE | 2458965 | 6/1976 |
|---|---|---|
| EP | 0019811 | 12/1980 |

(Continued)

OTHER PUBLICATIONS

Alonso, M. et al., "GSK-3 Inhibitors: Discoveries and Develoments", Current Medicinal Chemistry, 11, 755-763 (2004).

(Continued)

*Primary Examiner* — Jeffrey Murray
(74) *Attorney, Agent, or Firm* — Rory C. Stewart

(57) ABSTRACT

This invention describes novel pyrazole compounds of formula III:

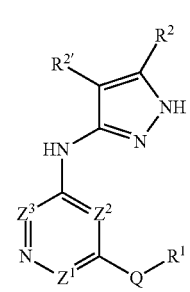

wherein $Z^1$, $Z^2$, and $Z^3$ are as described in the specification; Q is —S—, —O—, —N($R^4$)—, or —CH($R^6$)—; $R^1$ is T-Ring D, wherein Ring D is a 5-7 membered monocyclic ring or 8-10 membered bicyclic ring selected from aryl, heteroaryl, heterocyclyl or carbocyclyl; and $R^2$ and $R^{2'}$ are as described in the specification. The compounds are useful as protein kinase inhibitors, especially as inhibitors of Aurora-2 and GSK-3, for treating diseases such as cancer, diabetes and Alzheimer's disease.

10 Claims, No Drawings

(56) References Cited

U.S. PATENT DOCUMENTS

| | | | |
|---|---|---|---|
| 6,593,326 B1 | 7/2003 | Bradbury et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,642,227 B2 | 11/2003 | Cao et al. | |
| 6,653,300 B2 | 11/2003 | Bebbington et al. | |
| 6,653,301 B2 | 11/2003 | Bebbington et al. | |
| 6,656,939 B2 * | 12/2003 | Bebbington et al. | 514/242 |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,743,791 B2 | 6/2004 | Cao et al. | |
| 6,838,464 B2 | 1/2005 | Pease et al. | |
| 6,841,579 B1 | 1/2005 | Plowman et al. | |
| 6,846,928 B2 | 1/2005 | Bebbington et al. | |
| 6,949,544 B2 | 9/2005 | Bethiel et al. | |
| 6,989,385 B2 | 1/2006 | Bebbington et al. | |
| 7,008,948 B2 | 3/2006 | Bebbington et al. | |
| 7,084,159 B2 | 8/2006 | Cao et al. | |
| 7,087,603 B2 | 8/2006 | Bebbington et al. | |
| 7,091,343 B2 | 8/2006 | Bebbington et al. | |
| 7,098,330 B2 | 8/2006 | Bebbington et al. | |
| 7,115,739 B2 | 10/2006 | Bebbington et al. | |
| 7,179,826 B2 | 2/2007 | Bebbington et al. | |
| 7,253,187 B2 | 8/2007 | Cao et al. | |
| 2001/0018436 A1 | 8/2001 | Cushing et al. | |
| 2002/0052386 A1 | 5/2002 | Armistead et al. | |
| 2002/0065270 A1 | 5/2002 | Moriarty et al. | |
| 2003/0004161 A1 | 1/2003 | Bebbington et al. | |
| 2003/0004164 A1 | 1/2003 | Bebbington et al. | |
| 2003/0022885 A1 | 1/2003 | Bebbington et al. | |
| 2003/0036543 A1 | 2/2003 | Bebbington et al. | |
| 2003/0055044 A1 | 3/2003 | Davies et al. | |
| 2003/0055068 A1 | 3/2003 | Bebbington et al. | |
| 2003/0064981 A1 | 4/2003 | Knegtel et al. | |
| 2003/0064982 A1 | 4/2003 | Davies et al. | |
| 2003/0069239 A1 | 4/2003 | Cai et al. | |
| 2003/0069248 A1 | 4/2003 | Chakravarty et al. | |
| 2003/0073687 A1 | 4/2003 | Bebbington et al. | |
| 2003/0078166 A1 | 4/2003 | Davies et al. | |
| 2003/0078275 A1 | 4/2003 | Bebbington et al. | |
| 2003/0083327 A1 | 5/2003 | Davies et al. | |
| 2003/0087922 A1 | 5/2003 | Bethiel et al. | |
| 2003/0092714 A1 | 5/2003 | Cao et al. | |
| 2003/0096813 A1 | 5/2003 | Cao et al. | |
| 2003/0096816 A1 | 5/2003 | Cao et al. | |
| 2003/0105090 A1 | 6/2003 | Bebbington et al. | |
| 2003/0144309 A1 | 7/2003 | Choon-Moon | |
| 2003/0171389 A1 | 9/2003 | Bemis et al. | |
| 2003/0187002 A1 | 10/2003 | Mortlock et al. | |
| 2003/0199526 A1 | 10/2003 | Choquette et al. | |
| 2003/0207873 A1 | 11/2003 | Harrington et al. | |
| 2003/0225073 A1 | 12/2003 | Bebbington et al. | |
| 2004/0002496 A1 | 1/2004 | Bebbington et al. | |
| 2004/0009974 A1 | 1/2004 | Bebbington et al. | |
| 2004/0009981 A1 | 1/2004 | Bebbington et al. | |
| 2004/0009996 A1 | 1/2004 | Moon et al. | |
| 2004/0023963 A1 | 2/2004 | Cao et al. | |
| 2004/0029857 A1 | 2/2004 | Hale et al. | |
| 2004/0097501 A1 | 5/2004 | Bebbington et al. | |
| 2004/0097531 A1 | 5/2004 | Ledeboer et al. | |
| 2004/0157893 A1 | 8/2004 | Bebbington et al. | |
| 2004/0214814 A1 | 10/2004 | Bebbington et al. | |
| 2004/0229875 A1 | 11/2004 | Cao et al. | |
| 2005/0004110 A1 | 1/2005 | Bebbington et al. | |
| 2005/0038023 A1 | 2/2005 | Bebbington et al. | |
| 2005/0234059 A1 | 10/2005 | Hale et al. | |
| 2006/0270660 A1 | 11/2006 | Charrier et al. | |

FOREIGN PATENT DOCUMENTS

| | | |
|---|---|---|
| EP | 0136976 | 4/1985 |
| EP | 0302312 A2 | 2/1989 |
| GB | 2052487 | 1/1981 |
| JP | 10-130150 | 5/1998 |
| JP | 2000-026421 | 1/2000 |
| JP | 06-65237 | 10/2007 |
| WO | 9208715 A1 | 5/1992 |
| WO | 9322681 A1 | 11/1993 |
| WO | 9509851 | 4/1995 |
| WO | 9515758 A1 | 6/1995 |
| WO | 9614843 | 5/1996 |
| WO | 9709325 A1 | 3/1997 |
| WO | 9719065 A1 | 5/1997 |
| WO | 9802434 A1 | 1/1998 |
| WO | 9811095 A1 | 3/1998 |
| WO | 9814450 A1 | 4/1998 |
| WO | 9816502 A1 | 4/1998 |
| WO | 9838171 | 9/1998 |
| WO | 9918781 A1 | 4/1999 |
| WO | 9941253 A1 | 8/1999 |
| WO | 9947154 A1 | 9/1999 |
| WO | 9962518 A1 | 12/1999 |
| WO | 9965897 A1 | 12/1999 |
| WO | 0012497 | 3/2000 |
| WO | 0021955 | 4/2000 |
| WO | 0038675 | 7/2000 |
| WO | 0039101 | 7/2000 |
| WO | 0039101 A1 | 7/2000 |
| WO | 0042029 A1 | 7/2000 |
| WO | 0059509 A1 | 10/2000 |
| WO | 0078757 | 12/2000 |
| WO | 0078757 A1 | 12/2000 |
| WO | 0112621 A1 | 2/2001 |
| WO | 0125220 | 4/2001 |
| WO | 0139777 A1 | 6/2001 |
| WO | 0140215 A1 | 6/2001 |
| WO | 0144242 | 6/2001 |
| WO | 0147879 A1 | 7/2001 |
| WO | 0160816 A1 | 8/2001 |
| WO | 0164655 A1 | 9/2001 |
| WO | 0174768 A2 | 10/2001 |
| WO | 0179198 A1 | 10/2001 |
| WO | 0228244 A2 | 1/2002 |
| WO | 0218345 | 3/2002 |
| WO | 0218346 A1 | 3/2002 |
| WO | 0222601 A1 | 3/2002 |
| WO | 0224667 | 3/2002 |
| WO | 0247690 | 6/2002 |
| WO | 0250065 A2 | 6/2002 |
| WO | 0250066 A2 | 6/2002 |
| WO | 0279197 A1 | 10/2002 |
| WO | 0400833 A1 | 12/2003 |
| WO | 0413140 A1 | 2/2004 |
| WO | 2008077086 | 6/2008 |

OTHER PUBLICATIONS

Anonymous, "Vertex Inhbitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-I-(2-cyanopheny1) triazenes into 3-Arylqu i nazol i n-4(3H) -ones with Formamide" J. Chem. Soc. Perkin Trans. I, 3765-2766 (1984).

Bischoff, J.R., et al., "A homologue of Drosophila aurora kinase is oncogenic and amplified in human colorectal cancers", The EMBO Journal, 17(11): 3052-3065 (1998).

Bischoff, J.R., et al., "The Aurora/Ipl1p kinase family: regulators of chromosome segregation and cytokinesis", Cell Biology, 9, 454-459 (1999).

Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).

Wolff, M.E., "Burger's Medicinal Chemistry and Drug Discovery," 5th ed., vol. 1: Principles and Practice, 975-977 (1995).

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2

(56) References Cited

OTHER PUBLICATIONS diabetes treatment," Expert Opinion on Investigational Drugs, 12(9): 1511-1519 (2003).
Harrington, E.A. et al., "VX-680, a potent and selective small-molecule inhibitor of the Aurora kinases, suppresses tumor growth in vivo," Nat. Med., 10(3): 262-267 (2004).
Heutink, P., "Untangling tau-related dementia", Hum. Mol. Genet., 9(6): 979-986 (2000).
Nigg, E.A., "Mitotic Kinases as Regulators of Cell Division and its Checkpoints," Nat. Rev. Mol. Cell Biol., 2: 21-32 (2001).
Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).
CAPLUS listing Accession No. 1994:292136, Nakajima, Y. et al., "Pyrazoles agricultural and horticultural bactericides," JP 06065237 (1994).
Database CA "Online!" Chemical Abstract Service, Columbus, OH, US; Kelarev, V.I. et al., "Synthesis of amino derivatives of 1,3,5-triazine containing 1,3-4-thiadiazole fragments," Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).
Douglas, et al., Introduction to Viral Disease, Cecil Textbook of Medicine, 20th Edition, vol. 2, 1739-1749 (1996).
Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997). 25 Ali, N.M. et al, Palladium-Catalyzed Cross Coupling Reactions of Arylboronic.
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
IUPAC Compendium of Chemical Terminology on a definition of "aliphatic compounds" found from http://www.chemsoc.org/chembytes/goldbook/index.htm (last visited on Nov. 18, 2007). 30 Glossary of Class Names of Organic Compounds and Reactive Intermediates Based.
Glossary of Class Names of Organic Compounds and Reactive Intermediates Based on Structure found from http://www.chem.qmul.ac.uk/iupac/class/index.html (last visited on Nov. 18, 2007).
Nomenclature found from http://www.cem.msu.edu/~reusch/VirtualText/nomen1.htm (last visited on Nov. 18, 2007).
Bokemeyer, D. et al., "Multiple intracellular MAP kinase signaling cascades", Kidney Int., 49, 1187-1198 (1996).
Anderson, N.G. et al., "Multiple intracellular MAP kinase signaling cascades", Nature, 343, 651-653 (1990).

Crews, C.M. et al., "The Primary Structure of MEK, a Protein Kinase That Phosphorylates the ERK Gene Product", Science, 258, 478-480 (1992).
Bjorbaek, C. et al, "Divergent Functional Roles for p90rsk Kinase Domains", J. Biol. Chem., 270(32), 18848-18552 (1995).
Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).
Raingeaud, J. et al., MMK3- and MMK6-Regulated Gene Expression is Mediated by p38 Mitogen-Activated Protein Kinase Signal Transduction Pathway, Mol. Cell. Biol., 16, 1247-1255 (1996).
Chen, R.N. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).
Moodie, S.A. et al., "Complexes of Ras-GTP with Raf-1 and Mitogen-Activated Protein Kinase Kinase", Science, 260 (5114), 1658-1661 (1993).
Frey, R.S. et al., "Involvement of Extracellular Signal-regulated Kinase 2 and Stress-activated Protein Kinase/Jun NTerminal Kinase Activation by Transforming Growth Factor β in the Negative Growth Control of Breast Cancer Cells", Cancer Res., 57, 628-633 (1997).
Sivaraman, V.S., et al., "Hyperexpression of Mitogen-activated Protein Kinase in Human Breast Cancer", J. Clin. Invest., 99(7), 1478-1483 (1997).
Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).
Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).
Namikawa, T. J., et al., "Akt/Protein Kinase B Prevents Injury-Induced Motoneuron Death and Accelerates Axonal Regeneration", J. of Neuroscience, 20(8), 2875-2986 (2000).
Molina, T.J. et al., "Profound block in thymocyte development in mice lacking p56lck", Nature, 357, 161-164 (1992).
Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).
Chapriot, B. et al., "Quinazolines: Combined type 3 and 4 phosphodiesterase Inhibitors", Bioorg. Med. Chem. Lett. 8 (20), 2891-2896 (1998).
Singh, S.P. et al., "Synthesis & Mass Spectra of Some Substituted 2-(2'Benzazolylamino)pyrimidines", Indian J. Chem. Sect. B, 22(1); 37-42 (1983).
Ti, J. et al., "Anticandidal activity of pyrimidine-peptide conjugates", J. Med. Chem., 23(8), 913-918 (1980).
Kretzschmar, E. et al., "Syntese von 2,6-disubstituienten 4-Hydroxy-5,6,7,8-tetrahydropyrido[4-3-d]pyrimidinen," Pharmazie, 43(7), 475-476 (1988).
Norman, M.H. et al., "Structure-Activity Relationships of a Series of Pyrrolo[3-2-d]pyrimidine Derivatives and Related Compounds as Neuropeptide Y5 Receptor Antagonists", J. Med. Chem., 43(22), 4288-4312(2000).
Nugent, R.A. et al., "Pyrimidine Thiotheters: A Novel Class of HIV-1 Reverse Transcriptase inhibitors with Activity Against BHAP-Resisrtant HIV," J. Med. Chem. 41, 3793-3803 (1998).
Myers, M.R. et al., "The synthesis and SAR of new 4-(N-alkyl-N-phenyl)amino-6,7-dimethoxyquinazolines and 4-(Nalkyl-N-phenyl-aminopyrazolo[3,4-d]pyrimidines, inhibitors of CSF-1R tyrosine kinase activity", Bioorg. Med. Chem. Lett, 7, 4, 421-424 (1997).
Agarwal, N. et al., "Suitably functionised pyrimidines as potential antimycotic agents", Bioorg. Med. Chem. Lett. 10, 8, 703-706 (2000).
Crespo, M.I., "Design, Synthesis and Biological Activities of New Thieno[3,2-d]pyrimidines as Selective Type 4 Phosphodiesterase Inhibitors," J. Med. Chem., 41 (21), 4021-4035 (1998).
Noell, C.W. et al., "Potential Purine Antagonists. XX. The Preparation and Reactions of Some Methylthiopurines", J. Am. Chem. Soc., 81(22), 5997-6007 (1959).
Lubbens, T. et al., "Design, synthesis, and structure-activity relationship studies of ATP analogues as DNA gyrase inhibitors", Bioorg. Med. Chem. Lett., 10, 8, 821-826 (2000).

(56) References Cited

OTHER PUBLICATIONS

D'Atri, G. et al., "Novel pyrimidine and 1,3,5-triazine hypolipemic agents", J. Med. Chem. 27 (12), 1621-1629 (1984).
Venugopalan, B. et al., "Synthesis and antimalarial activity of pyrido[3-2-f]quinozalines and their oxides", Indian J. Chem. Sect. B, 34, 9, 778-790 (1995).
Curd F.H.S. et al., "Syntetic antimalarials. Part XVII. Some aminoalylaminoquinoline derivatives", J. Chem. Soc. 899-909 (1947).
Haworth, R.D. et al., "Synthetic antimalarials. Part XXVII. Some derivatives of phthalazine, quinozaline, and isoquinoline," J. Chem. Soc., 777-782 (1948).
Nair, M.D., et al., "3-Chloroisocarbostyril & Its Chlorination Products," Indian J. Chem., 467-470 (1967).
Jeffery, J.E. et al., "Synthesis of sibutramine, a novel byclobutylalkylamine useful in the treatment of obesity, and its major human metabolites", J. Chem. Soc., Perkins Trans. 1, 21, 2583-2589 (1996).
Gnecco, D. et al., "An Improved Preparation of 1-Methyl-4-Cyano-4-phenylpiperidine", Org. Prep. Proced. Int., 18 (4), 478-480 (1996).
Fedorynski, M. et al., "Synthesis of 1-Arycyclopropanecarbonitriles under Phase-transfer Catalytic Conditions", Org. Prep. Proced. Int., 27(3), 355-359 (1995).
Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).
Prasad, G. et al, "18-Crown-6 as a catalyst in the dialkylation of o-nitrophenacyl derivatives", J. Org. Chem., 25, 7188-7199 (1991).
Moss, R.A. et al., "Conversion of 'Obstinate' Nitriles to Amidines by Garigipati's Reaction", Tetrahedron Lett., 36(48), 8761-8764 (1995).
Garigipati, R.S., "An efficient conversion of nitriles to amidines", Tetrahedron Lett., 31(14), 1969-1972 (1990).
Cohen, P. "Dissection of the Protein Phosphorylation Cascades Involved in Insulin and Growth Factor Action", Biochem. Soc. Trans., 21, 555-567 (1983).
Haq, S., "Glycogen Synthase Kinase-3β is a Negative Regulator of Cardiomyocyte Hypertrophy", J. Cell Biol., 151(1), 117-129 (2000).
Fischer, P.M. et al., "Inhibitors of Cyclin-Dependent Kinases as Anti-Cancer Therapeutics", Current Med. Chem., 7, 1213-1245 (2000).
Mani, S. et al., "Cyclin-dependent kinase: novel anticancer agents", Exp. Opin. Invest. Drugs., 8, 1849-1870 (2000).
Fry, D.W. et al., "Inhibitors of cyclin-dependent kinases as therapeutic agents for the treatment of cancer", Current Opin. Oncol. Endoc. & Metab. Investig., 2-40-59 (2000).
Wiener, J.R. et al., "Decreased Src Tyrosine Kinase Activity Inhibits Malignant Human Ovarian Cancer Tumor Growth in a Nude Mouse Model," Clinical Cancer Research, 5, 2164-2170 (1999).
Warner, S.L. et al., "Targeting Aurora-2 Kinase in Cancer," Mol. Cancer Thera., 2, 589-585, 2003.
Wagman, A.S. et al., "Discovery and Development of GSK3 Inhibitors for the Treatment of Type 2 Diabetes," Current Pharmaceutical Design, 10, 1104-1137 (2004.
Nezu, Y. et al., "Dimethoxypyrimidines as Novel Herbicides. Part 2, Synthesis and Herbicidal Activity of Dimelhoxyphenoxyphenoxypyrimidines and Analogues," Pestic. Sci., 47: 115-124 (1996).
Tanaka, T.U. et al., "Evidence that the Ipl1-Sil (Aurora Kinase-INCENP) Complex Promotes Chromosome Biorientation by Altering Kinetochore-Spindle Pole Connections," Cell, 108, 317-329 (2002).
Staley, C.A. et al., "Decreased Tumorigenicity of a Human Colon Adenocarcinoma Cell: Line by an Antisense Expression Vector Specific for c-SRc" Cell Growth & Differentiation, 8:269-274 (1997).
Soriano, P. et al., "Targed Disruption of the C-SIC Pmto-Oncogene Leads to Osteopetrosis in Mice," Cell, 64: 693-702 (1991).

Campbell, S.F. et al., "2,4-Diamino-6,7-dimethoxyquinazolines, 3.2 (4-Heterocyclypiperzin-l-yl) Derivatives as α1-Adrenoceptor Antagonists and Antihypertensive Agents," J. Med. Chem., 30, 1794-1978 (1987).
Casanova, B., et al., "Revision critica de la patogenia actual de la esclerosis multiple y futuras direcciones posibles," Rev. Neurol., 28 (9): 909-915 (1999).
Cline G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Simone, J.V., "Oncology: Introduction" in Cecil Textbook in Medicine, 20th ed., vol. 1, 1004-1010 (1996).
Coleman, R.A., "The Biological Evaulation of New Compounds" in Medicinal Chemistry: Principles and Practice, King, Frank D. ed, Royal Society of Chemistry, 53-66 (1994).
The Condensed Chemical Dictionary, Sixth Edition by Arthur and Elizabeth Rose, 38 (1961).
Damasio, A.R., "Alzheimer's Disease and Related Dementia," in Cecil Textbook of Medicine, 20th ed., 2: 1992-1996 (1996).
Rogers, E. et al., "The aurora kinase AIR-2 functions in the release of chromosome cohesion in *Caenorhabditis elegans* meiosis," J. Cell Biol., 157(2): 219-229 (2002).
Fisher A., "Therapeutic Strategies in Alzheimer's Disease: M1 Muscarinic Agonists," Jpn. J. Pharmacol., 84(2):101-12 (2000).
Frame, M.C., "Src in cancer: deregulation and consequences for cell behaviour," Biochimica et Biophysics Acta 1602, Biochim Biophys Acta. Jun. 21, 2002;1602(2):114-30.
Frampton, J.E. et al., "Pentoxifyline (Oxpentifyline)—A Review of its Therapeutic Efficacy in the Management of Peripheral Vascular and Cerebrovascular Disorder," Drugs & Aging, 7(6): 480-5003 (1995).
Ganellin, C.R., "Past Approaches to Discovering New Drugs as Medicines" in Medicinal Chemistry, Principles and Practices. King, Frank D. ed, Royal Society of Chemistry, 189-205 (1994).
Hamdane, M. et al., "A Therapeutic Target in Alzheimer Neurodegeneration," J. Mol. Neurosci., 19(3): 275-87 (2002).
Hardt, S.E. et al., "Glycogen Synthase Kinase-3β—A Novel Regulator of Cardiac Hypertrophy and Development," Circulation Research, 90: 1055-1063 (2002).
Pamell, E.W., "2-Cyano-4-nitrophenythydrazine and 3-Amino-5-nitroindazole", J. Chem. Soc., 2363-2365 (1959).
Heaney F. et al., "Pyrimidine annelated heterocycles-synthesis and cycloaddition of the first pyrimido[1,4]diazepine Noxides," J. Chem. Soc., Perkin Trans. 1, 622-632 (2001).
Hendriksen, E.J. et al., "Modulation of muscle insulin resistance by selective inhibition of GSK-3 in Zucker diabetic fatty rats," Am. J. Physiol. Endocrinol. Metab., 284: E892-E900 (2003).
Okafor, C.O., "Studies in the Heterocyclic Series, X. 1,3,9-Triazaphenothiazine Ring System, a new Phenothiazine Ring," J. Org. Chem., 40(19): 2753-2755 (1975).
Jambhekar, S.S., "Biopharmaceutical Properties of Drug Sustances" in Principles of Medicinal Chemistry, 4th ed., 12-24, (1995).
Layzer, R.B., "Section Five—Degenerative Diseases of the Nervous System" in Cecil Textbook of Medicine, 20th ed., 2: 2050-2057 (1996).
Lee, S.J. et al., "Discovery of Potent Cyclic GMP Phosphodiesterase Inhibitors. 2-Pyridyl- and 2-Imidazolylquninazolines Possessing Cyclic GMP Phosphodiesterase and Thromboxane Synthesis Inhibitory Activities," J. Med. Chem., 38 (18): 3547-3557 (1995).
Medwid, J.B. et al., "Preparation of Triazolo[1,5-]pyrimidines as Potential Antiasthma Agents," J. Med Chem. 33, 1230-1241 (1990).
Nezu Y. et al. "Dimethoxypyrimidines as Novel Herbicides. Part 1. Synthesis and Herbicidal Activity of Dimethoxyphenoxyphenoxypyrimidines and Analogues," Pestic. Sci. 47: 103-113 (1996).
Coghlan et al., "Selective small molecule inhibitors of glycogen synthase kinase-3 modulate glycogen metabolism and gene transcription," Chemistry & Biology, 7, 793-83 (2000).
Klein, et al. "A molecular mechanism for the effect of lithium on development", PNAS, 93:8455-8459 (1996).
Cross et al., "The inhibition of glycogen synthase kinase-3 by insulin or insulin-like growth factor 1 in the rat skeletal muscle cell line L6 is blocked by wortmannin, but not by rapamycin: evidence that

(56) References Cited

OTHER PUBLICATIONS wortmannin blocks activation of the mitogen-activation of the mitogen-activated protein kinase pathway in L6 cells between Ras and Raf", Biochem J., 303: 21-26 (1994).

Massilion et al., "Identification of the glycogenic compounds 5-iodotubercidin as a general protein kinase inhibitor", Biochem J., 299: 123-128 (1994).

Fox T. et al., "A single amino acid substitution makes ERK2 susceptible to pyridinyl imidazole inhibitors of p38 MAP kinase", Protein Sci., 7: 2249-2255 (1998).

Takayangi, H. et al., "Suppression of arthritic bone destruction by adenovirus-mediated csk gene transfer to synoviocytes and osteoclasts", J. Clin. Invest., 104, 137-146 (1999).

Boschelli et al., "Small molecule inhibitors of Src family kinases", Drugs of the Future, 25(7): 717-736 (2000).

Talamonti, M.S. et al., "Increase in activity and level of pp60c-src in progressive stages of human colorectal cancer", J. Clin Invest, 91(1):53-60 (1993).

Lutz, M.L. et al., "Overexpression and Activation of the Tyrosine Kinase Src in Human Pancreatic Carcimona", Biochem. Biophys. Res. 243 503-508 (1998).

Rosen, N. et al., "Analysis of pp60c-src Protein Kinase Activity in Human Tumor Cell Lines and Tissues", J. Biol. Chem., 261, 13754-13759 (1986).

Bolen, J.B. et al. "Activation of pp60c-src protein kinase activity in human colon carcinoma", PNAS, 84, 2251-2255 (1987).

Masaki, T. et al. "pp60-src Activation in Hepatocellular Carcinoma of Humans and LEC Rats", Hapatology, 27, 1257 (1998).

Biscardi, J.S. et al., "c-Src, Receptor Tyrosine Kinase, and Human Cancer", Adv. Cancer Res., 76 61 (1999).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Singhal. N. et al., "Synthesis and Antimalarial Activity of Some New Quinazoline Derivatives", Indian Chem. Soc., 61, 690-693 (1984).

Kim, Y.Z. et al., "Synthesis and Antimicrobial Activity of Novel [(3-Aminopyrimidiniumyl)thio]methyl Cephalosporins", J. Med. Chem. 37(22): 3828-3833 (1994).

Rueeger, H. et al., "Design, synthesis and SAR of a series of 2-substituted 4-1mino-quinazoline neuropeptide Y Y5 receptor antagonists", Bioorg. Med. Chem. Lett., 10(11), 1175-1180 (2000).

Gershon, H. et al., "Pyrimidines. 7. A Study of the Chlorination of Pyrimidines with Phosphorus Oxychloride in the Presence of N, N-Dimethylaniline", J. Heterocyclic Chem., 21, 1161 (1984).

Ife, R.J. et al., "Reversible Inhibitors of the Gastric (H+/K+-ATPase. 5. Substituted 2,4-Diaminoquinazolines and Thienopyrimidines", J. Med. Chem., 38 (14); 2763-2773 (1995).

Tanzi, K. et al., "Purines. X. Reactives of Methyl Groups on 9-Phenylpurines: Condensation with an Aldehyde or an Ester, and Oxidation with Selenium Dioxide", Chem. Phar. Bull., 40 (1), 227-229 (1992).

* cited by examiner

PYRAZOLE COMPOUNDS USEFUL AS PROTEIN KINASE INHIBITORS

RELATED APPLICATIONS

This application is a continuation application of U.S. patent application Ser. No. 12/109,598, filed Apr. 25, 2008, which is a continuation application of U.S. patent application Ser. No. 10/775,699, filed Feb. 10, 2004, now U.S. Pat. No. 7,427,681, which is a divisional application of U.S. patent application Ser. No. 10/034,019, filed Dec. 20, 2001, now U.S. Pat. No. 6,727,251, which claims the benefit, under 35 U.S.C. §119 of U.S. Provisional Patent Application 60/257,887 filed Dec. 21, 2000 and U.S. Provisional Patent Application 60/286,949 filed Apr. 27, 2001, the contents of which are incorporated herein by reference.

FIELD OF THE INVENTION

The present invention is in the field of medicinal chemistry and relates to compounds that are protein kinase inhibitors, compositions containing such compounds and methods of use. More particularly, this invention relates to compounds that are inhibitors of Aurora-2 protein kinase. The invention also relates to methods of treating diseases associated with protein kinases, especially diseases associated with Aurora-2, such as cancer.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor $\alpha$ (TNF-$\alpha$)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Aurora-2 is a serine/threonine protein kinase that has been implicated in human cancer, such as colon, breast and other solid tumors. This kinase is believed to be involved in protein phosphorylation events that regulate the cell cycle. Specifically, Aurora-2 may play a role in controlling the accurate segregation of chromosomes during mitosis. Misregulation of the cell cycle can lead to cellular proliferation and other abnormalities. In human colon cancer tissue, the aurora-2 protein has been found to be overexpressed. See Bischoff et al., *EMBO J.*, 1998, 17, 3052-3065; Schumacher et al., *J. Cell Biol.*, 1998, 143, 1635-1646; Kimura et al., *J. Biol. Chem.*, 1997, 272, 13766-13771.

Glycogen synthase kinase-3 (GSK-3) is a serine/threonine protein kinase comprised of $\alpha$ and $\beta$ isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor $\beta$-catenin, the translation initiation factor e1F2B, as well as ATP citrate lyase, axin, heat shock factor-1, c-Jun, c-Myc, c-Myb, CREB, and CEPB$\alpha$. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase.

The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); Massillon et al., *Biochem J.* 299, 123-128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known $\beta$-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077-86 (1994); Brownlees et al., *Neuroreport* 8, 3251-55 (1997)]. Therefore, it is believed that GSK-3 activity may promote generation of the neurofibrillary tangles and the progression of Alzheimer's disease.

Another substrate of GSK-3 is $\beta$-catenin which is degradated after phosphorylation by GSK-3. Reduced levels of $\beta$-catenin have been reported in schizophrenic patients and have also been associated with other diseases related to increase in neuronal cell death [Zhong et al., *Nature*, 395, 698-702 (1998); Takashima et al., *PNAS,* 90, 7789-93 (1993); Pei et al., *J. Neuropathol. Exp,* 56, 70-78 (1997)].

As a result of the biological importance of GSK-3, there is current interest in therapeutically effective GSK-3 inhibitors. Small molecules that inhibit GSK-3 have recently been reported [WO 99/65897 (Chiron) and WO 00/38675 (Smith-Kline Beecham)].

For many of the aforementioned diseases associated with abnormal GSK-3 activity, other protein kinases have also been targeted for treating the same diseases. However, the various protein kinases often act through different biological pathways. For example, certain quinazoline derivatives have been reported recently as inhibitors of p38 kinase (WO 00/12497 to Scios). The compounds are reported to be useful for treating conditions characterized by enhanced p38-α activity and/or enhanced TGF-β activity. While p38 activity has been implicated in a wide variety of diseases, including diabetes, p38 kinase is not reported to be a constituent of an insulin signaling pathway that regulates glycogen synthesis or glucose uptake. Therefore, unlike GSK-3, p38 inhibition would not be expected to enhance glycogen synthesis and/or glucose uptake.

There is a continued need to find new therapeutic agents to treat human diseases. The protein kinases Aurora-2 and GSK-3 are especially attractive targets for the discovery of new therapeutics due to their important roles in cancer and diabetes, respectively.

DESCRIPTION OF THE INVENTION

It has now been found that compounds of this invention and pharmaceutical compositions thereof are effective as protein kinase inhibitors, particularly as inhibitors of Aurora-2. These compounds have the general formula I:

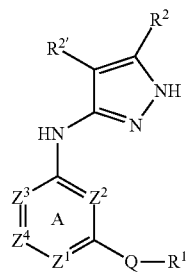

I or a pharmaceutically acceptable derivative or prodrug thereof, wherein:

$Z^1$ to $Z^4$ are as described below;

Ring A is selected from the group consisting of:

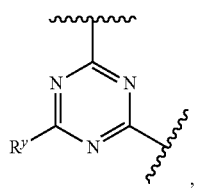

a

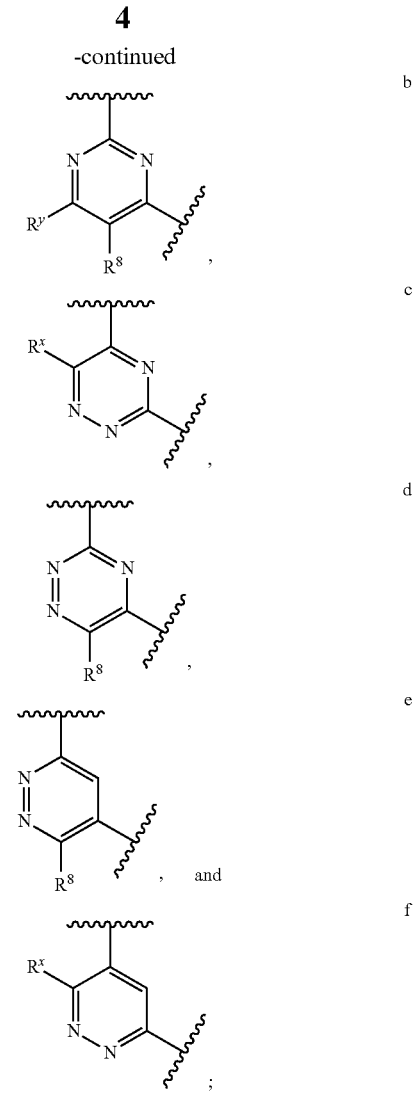

$R^x$ is T-$R^3$ or L-Z—$R^3$;

$R^y$ is Z—$R^{3'}$ or an optionally substituted group selected from $C_{1-6}$ aliphatic, $C_{6-10}$ aryl, a heteroaryl ring having 5-10 ring atoms, or a heterocyclyl ring having 5-10 ring atoms, or $R^y$ and $R^8$ are taken together to form a fused, optionally substituted 5-7 membered, unsaturated or partially unsaturated, ring having 0-3 ring heteroatoms selected from nitrogen, oxygen, or sulfur;

Q is selected from —N($R^4$)—, —O—, —S—, or —CH($R^6$)—;

$R^1$ is T-(Ring D);

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;

T is a valence bond or a $C_{1-4}$ alkylidene chain, wherein when Q is —CH($R^6$)—, a methylene unit of said $C_{1-4}$ alkylidene chain is optionally replaced by —O—, —S—, —N($R^4$)—, —CO—, —CONH—, —NHCO—, —$SO_2$—, —$SO_2$NH—, —$NHSO_2$—, —$CO_2$—, —OC(O)—, —OC(O)NH—, or —$NHCO_2$—;

Z is a $C_{1-4}$ alkylidene chain;

L is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

R$^2$ and R$^{2'}$ are independently selected from —R, -T-W—R$^6$, or R$^2$ and R$^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by R$^2$ and R$^{2'}$ is independently substituted by halo, oxo, —CN, —NO$_2$, —R$^7$, or —V—R$^6$, and each substitutable ring nitrogen of said ring formed by R$^2$ and R$^{2'}$ is independently substituted by R$^4$;

R$^3$ is selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$(C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

R$^{3'}$ is selected from -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R)CO$_2$(C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, —OC(=O)N(R$^7$)$_2$, or an optionally substituted group selected from C$_{1-16}$ aliphatic, C$_{6-10}$ aryl, a heteroaryl ring having 5-10 ring atoms, or a heterocyclyl ring having 5-10 ring atoms;

each R is independently selected from hydrogen or an optionally substituted group selected from C$_{1-6}$ aliphatic, C$_{6-10}$ aryl, a heteroaryl ring having 5-10 ring atoms, or a heterocyclyl ring having 5-10 ring atoms;

each R$^4$ is independently selected from —R$^7$, —COR$^7$, —CO$_2$ (optionally substituted C$_{1-6}$ aliphatic), —CON(R$^7$)$_2$, or —SO$_2$R$^7$;

each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen or an optionally substituted C$_{1-4}$ aliphatic group, or two R$^6$ groups on the same nitrogen atom are taken together with the nitrogen atom to form a 5-6 membered heterocyclyl or heteroaryl ring;

each R$^7$ is independently selected from hydrogen or an optionally substituted C$_{1-6}$ aliphatic group, or two R$^7$ on the same nitrogen are taken together with the nitrogen to form a 5-8 membered heterocyclyl or heteroaryl ring; and R$^8$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$.

As used herein, the following definitions shall apply unless otherwise indicated. The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "aliphatic" as used herein means straight-chain, branched or cyclic C$_1$-C$_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C$_3$-C$_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O)CH(V—R°)(R°); wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0-6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon are within the scope of this invention.

Compounds of formula I or salts thereof may be formulated into compositions. In a preferred embodiment, the composition is a pharmaceutical composition. In one embodiment, the composition comprises an amount of the protein kinase inhibitor effective to inhibit a protein kinase, particularly Aurora-2, in a biological sample or in a patient. In another embodiment, compounds of this invention and pharmaceutical compositions thereof, which comprise an amount of the protein kinase inhibitor effective to treat or prevent an Aurora-2-mediated condition and a pharmaceutically acceptable carrier, adjuvant, or vehicle, may be formulated for administration to a patient.

Another aspect of this invention relates to a method of treating or preventing an Aurora-2-mediated disease with an Aurora-2 inhibitor, which method comprises administering to a patient in need of such a treatment a therapeutically effective amount of a compound of formula I or a pharmaceutical composition thereof.

The term "Aurora-2-mediated condition" or "disease", as used herein, means any disease or other deleterious condition in which Aurora is known to play a role. The term "Aurora-2-mediated condition" or "disease" also means those diseases or conditions that are alleviated by treatment with an Aurora-2 inhibitor. Such conditions include, without limitation, cancer. The term "cancer" includes, but is not limited to the following cancers: colon, breast, stomach, and ovarian.

Another aspect of the invention relates to inhibiting Aurora-2 activity in a biological sample, which method comprises contacting the biological sample with the Aurora-2 inhibitor of formula I, or a composition thereof.

Another aspect of this invention relates to a method of inhibiting Aurora-2 activity in a patient, which method comprises administering to the patient a compound of formula I or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula I or a pharmaceutical composition thereof.

The term "GSK-3-mediated condition" or "disease", as used herein, means any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a GSK-3 inhibitor of formula I.

Another aspect of this invention relates to a method of inhibiting GSK-3 activity in a patient, which method comprises administering to the patient a compound of formula I or a composition comprising said compound.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The amount effective to inhibit protein kinase, for example, Aurora-2 and GSK-3, is one that measurably inhibits the kinase activity where compared to the activity of the enzyme in the absence of an inhibitor. Any method may be used to determine inhibition, such as, for example, the Biological Testing Examples described below.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives or prodrugs of the compounds of this invention may also be employed in compositions to treat or prevent the above-identified diseases or disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase-mediated condition to be treated or prevented, additional therapeutic agents, which are normally administered to treat or prevent that condition, may be administered together with the inhibitors of this invention. For example, in the treatment of cancer other chemotherapeutic agents or other anti-proliferative agents may be combined with the Aurora-2 inhibitors of this invention to treat cancer. These agents include, without limitation, adriamycin, dexamethasone, vincristine, cyclophosphamide, fluorouracil, topotecan, taxol, interferons, and platinum derivatives.

Other examples of agents the inhibitors of this invention may also be combined with include, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

Compounds of this invention may exist in alternative tautomeric forms, as in tautomers i and ii shown below. Unless otherwise indicated, the representation of either tautomer is meant to include the other.

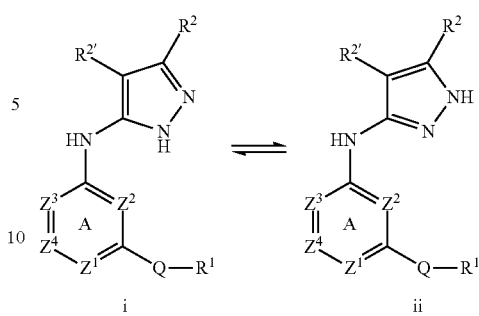

Preferred $R^x$ groups, when present, include hydrogen, alkyl- or dialkylamino, acetamido, or a $C_{1-4}$ aliphatic group such as methyl, ethyl, cyclopropyl, or isopropyl.

Preferred $R^y$ groups, when present, include Z—$R^{3'}$ or an optionally substituted group selected from $C_{1-6}$ aliphatic, 5-6 membered heterocyclyl, phenyl, or 5-6 membered heteroaryl, wherein Z is a methylene and $R^{3'}$ is —$N(R^4)_2$, —OR, or an optionally substituted group selected from $C_{1-6}$ aliphatic, $C_{6-10}$ aryl, a heteroaryl ring having 5-ring atoms, or a heterocyclyl ring having 5-10 ring atoms. Preferred $R^y$ groups include 5-6 membered heteroaryl or heterocyclyl rings, such as 2-pyridyl, 4-pyridyl, pyrrolidinyl, piperidinyl, morpholinyl, or piperazinyl; $C_{1-6}$ aliphatic, such as methyl, ethyl, cyclopropyl, isopropyl, or t-butyl; alkoxyalkylamino such as methoxyethylamino; alkoxyalkyl such as methoxymethyl or methoxyethyl; alkyl- or dialkylamino such as ethylamino or dimethylamino; alkyl- or dialkylaminoalkoxy such as dimethylaminopropyloxy; acetamido; and optionally substituted phenyl such as phenyl or halo-substituted phenyl.

$R^2$ and $R^{2'}$ may be taken together to form a fused ring, thus providing a bicyclic ring system containing a pyrazole ring. Preferred fused rings include benzo, pyrido, pyrimido, and a partially unsaturated 6-membered carbocyclo ring, wherein said fused ring is optionally substituted. These are exemplified in the following formula I compounds having a pyrazole-containing bicyclic ring system:

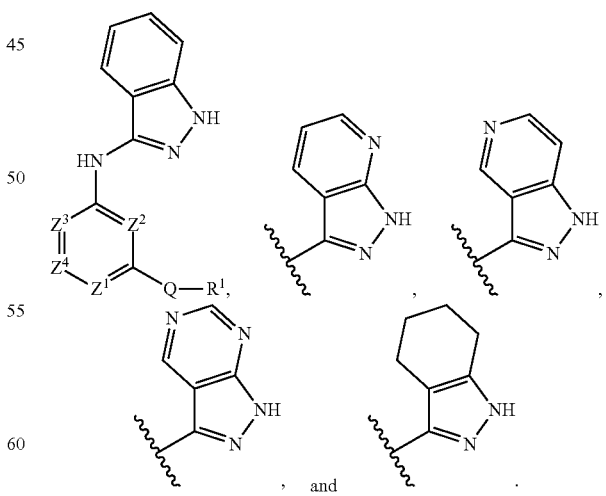

Preferred substituents on the $R^2/R^{2'}$ fused ring include one or more of the following: -halo, —$N(R^4)_2$, —$C_{1-3}$ alkyl, —$C_{1-3}$ haloalkyl, —$NO_2$, —$O(C_{1-3}$ alkyl), —$CO_2(C_{1-3}$ alkyl), —CN, —$SO_2(C_{1-3}$ alkyl), —$SO_2NH_2$, —$OC(O)NH_2$, —NH₂SO₂(C₁₋₃ alkyl), —NHC(O) (C₁₋₃ alkyl), —C(O)NH₂, and —CO(C₁₋₃ alkyl), wherein the (C₁₋₃ alkyl) is most preferably methyl.

When the pyrazole ring system is monocyclic, preferred R² groups include hydrogen, C₁₋₄ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred R² substituents include methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃)CH₂Ph, CONH(n-C₃H₇), CON(Et)CH₂CH₂CH₃, CONHCH₂CH(CH₃)₂, CON (n-C₃H₇)₂, CO (3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl). A preferred R²' group is hydrogen.

Preferred Q groups of formula I include —S—, —NH—, and —CH₂—. More preferred Q groups of formula I include —S— and —NH—.

Another embodiment of this invention relates to compounds of formula II:

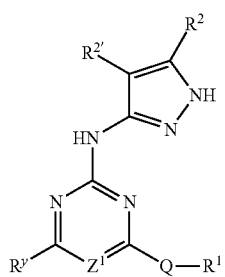

II or a pharmaceutically acceptable derivative or prodrug thereof, wherein:

Z¹ is nitrogen or CR⁸;

Rʸ is Z—R³' or an optionally substituted group selected from C₁₋₆ aliphatic, C₆₋₁₀ aryl, a heteroaryl ring having 5-10 ring atoms, or a heterocyclyl ring having 5-10 ring atoms, or Rʸ and R⁸ are taken together to form a fused, optionally substituted 5-7 membered, unsaturated or partially unsaturated, ring having 0-3 ring heteroatoms selected from nitrogen, oxygen, or sulfur;

Q is selected from —N(R⁴)—, —O—, —S—, or —CH(R⁶)—;

R¹ is T-(Ring D);

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-R⁵, or V—Z—R⁵, and each substitutable ring nitrogen of Ring D is independently substituted by —R⁴;

T is a valence bond or a C₁₋₄ alkylidene chain, wherein when Q is —CH(R⁶)—, a methylene unit of said C₁₋₄ alkylidene chain is optionally replaced by —O—, —S—, —N(R⁴)—, —CO—, —CONH—, —NHCO—, —SO₂—, —SO₂NH—, —NHSO₂—, —CO₂—, —OC(O)—, —OC(O)NH—, or —NHCO₂—;

Z is a C₁₋₄ alkylidene chain;

L is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

R² and R²' are independently selected from —R, -T-W—R⁶, or R² and R²' are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by R² and R²' is independently substituted by halo, oxo, —CN, —NO₂, —R⁷, or —V—R⁶, and each substitutable ring nitrogen of said ring formed by R² and R²' is independently substituted by R⁴;

R³' is selected from -halo, —OR, —C(=O)R, —CO₂R, —COCOR, —COCH₂COR, —NO₂, —CN, —S(O)R, —S(O)₂R, —SR, —N(R⁴)₂, —CON(R⁷)₂, —SO₂N(R⁷)₂, —OC(=O)R, —N(R⁷)COR, —N(R⁷)CO₂(C₁₋₆ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, —OC(=O)N(R⁷)₂, or an optionally substituted group selected from C₁₋₆ aliphatic, C₆₋₁₀ aryl, a heteroaryl ring having 5-10 ring atoms, or a heterocyclyl ring having 5-10 ring atoms;

each R is independently selected from hydrogen or an optionally substituted group selected from C₁₋₆ aliphatic, C₆₋₁₀ aryl, a heteroaryl ring having 5-10 ring atoms, or a heterocyclyl ring having 5-10 ring atoms;

each R⁴ is independently selected from —R⁷, —COR⁷, —CO₂ (optionally substituted C₁₋₆ aliphatic), —CON(R⁷)₂, or —SO₂R⁷;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂ (optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted C₁₋₄ aliphatic group, or two R⁶ groups on the same nitrogen atom are taken together with the nitrogen atom to form a 5-6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5-8 membered heterocyclyl or heteroaryl ring; and $R^8$ is selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$; provided that when Q is —NH— and $R^y$ and $R^8$ are taken together to form a fused ring, $R^1$ is other than a pyrazol-3-yl ring or a pyrazol-3-yl-containing bicyclic ring system.

Another embodiment of this invention relates to compounds of formula IIa:

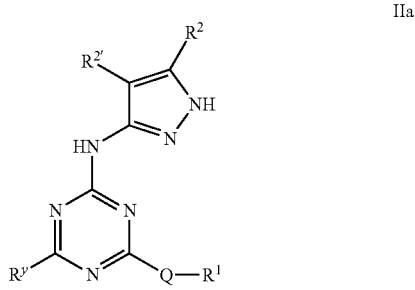

IIa or a pharmaceutically acceptable derivative or prodrug thereof, wherein:

$R^y$ is Z—$R^{3'}$ or an optionally substituted group selected from $C_{1-6}$ aliphatic, $C_{6-10}$ aryl, a heteroaryl ring having 5-10 ring atoms, or a heterocyclyl ring having 5-10 ring atoms;

Q is selected from —$N(R^4)$—, —O—, —S—, or —CH($R^6$)—;

$R^1$ is T-(Ring D);

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;

T is a valence bond or a $C_{1-4}$ alkylidene chain, wherein when Q is —CH($R^6$)—, a methylene unit of said $C_{1-4}$ alkylidene chain is optionally replaced by —O—, —S—, —$N(R^4)$—, —CO—, —CONH—, —NHCO—, —$SO_2$—, —$SO_2NH$—, —$NHSO_2$—, —$CO_2$—, —OC(O)—, —OC(O)NH—, or —$NHCO_2$—;

Z is a $C_{1-4}$ alkylidene chain;

L is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —OC(O)$N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, or —$C(R^6)_2N(R^6)CON(R^6)$—;

$R^2$ and $R^{2'}$ are independently selected from —R, -T-W—$R^6$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by $R^4$;

$R^{3'}$ is selected from -halo, —OR, —C(=O)R, —$CO_2R$, —COCOR, —$COCH_2COR$, —$NO_2$, —CN, —S(O)R, —$S(O)_2R$, —SR, —$N(R^4)_2$, —$CON(R^7)_2$, —$SO_2N(R^7)_2$, —OC(=O)R, —$N(R^7)COR$, —$N(R^7)CO_2(C_{1-6}$ aliphatic), —$N(R^4)N(R^4)_2$, —C=$NN(R^4)_2$, —C=N—OR, —$N(R^7)CON(R^7)_2$, —$N(R^7)SO_2N(R^7)_2$, —$N(R^4)SO_2R$, —OC(=O)$N(R^7)_2$, or an optionally substituted group selected from $C_{1-6}$ aliphatic, $C_{6-10}$ aryl, a heteroaryl ring having 5-10 ring atoms, or a heterocyclyl ring having 5-10 ring atoms;

each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;

each $R^4$ is independently selected from —$R^7$, —$COR^7$, —$CO_2$ (optionally substituted $C_{1-6}$ aliphatic), —$CON(R^7)_2$, or —$SO_2R^7$;

each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —OC(O)$N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, or —$C(R^6)_2N(R^6)CON(R^6)$—;

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$CO_2$—, —$C(R^6)OC(O)$—, —$C(R^6)OC(O)N(R^6)$—, —$C(R^6)_2N(R^6)CO$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, —$C(R^6)_2N(R^6)CON(R^6)$—, or —$CON(R^6)$—;

each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5-8 membered heterocyclyl or heteroaryl ring.

Preferred $R^y$ groups of formula IIa include Z—$R^{3'}$ or an optionally substituted group selected from $C_{1-6}$ aliphatic, 5-6 membered heterocyclyl, phenyl, or 5-6 membered heteroaryl, wherein Z is a methylene and $R^{3'}$ is —$N(R^4)_2$, —OR, or an optionally substituted group selected from $C_{1-6}$ aliphatic, $C_{6-10}$ aryl, a heteroaryl ring having 5-10 ring atoms, or a heterocyclyl ring having 5-10 ring atoms.

Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The $R^2$ and $R^{2'}$ groups of formula IIa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIa compounds having a pyrazole-containing bicyclic ring system:

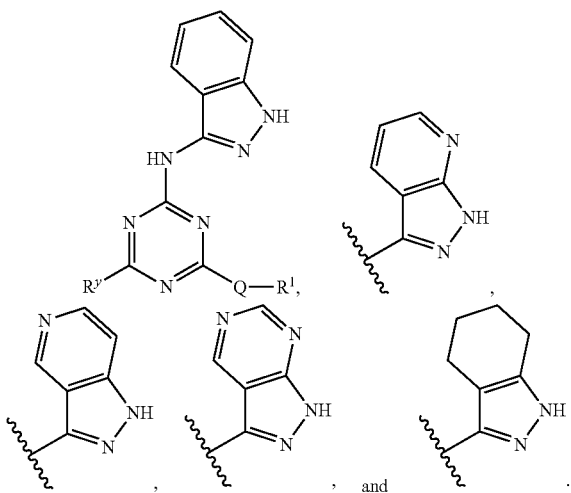

Preferred substituents on the $R^2/R^{2'}$ fused ring of formula IIa include one or more of the following: -halo, —N($R^4$)$_2$, —$C_{1-4}$ alkyl, —$C_{1-4}$ haloalkyl, —NO$_2$, —O($C_{1-4}$ alkyl), —CO$_2$($C_{1-4}$ alkyl), —CN, —SO$_2$($C_{1-4}$ alkyl), —SO$_2$NH$_2$, —OC(O)NH$_2$, —NH$_2$SO$_2$($C_{1-4}$ alkyl), —NHC(O) ($C_{1-4}$ alkyl), —C(O)NH$_2$, and —CO($C_{1-4}$ alkyl), wherein the ($C_{1-4}$ alkyl) is a straight, branched, or cyclic alkyl group. Preferably, the ($C_{1-4}$ alkyl) group is methyl.

When the pyrazole ring system of formula IIa is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIa is monocyclic, preferred Ring D groups include phenyl, pyridyl, pyridazinyl, pyrimidinyl, and pyrazinyl.

When Ring D of formula IIa is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIa, preferred T-$R^5$ or V—Z—$R^5$ substituents include -halo, —CN, —NO$_2$, —N($R^4$)$_2$, optionally substituted $C_{1-6}$ aliphatic group, —OR, —C(O)R, —CO$_2$R, —CONH($R^4$), —N($R^4$)COR, —N($R^4$)CO$_2$R, —SO$_2$N($R^4$)$_2$, —N($R^4$)SO$_2$R, —N($R^6$)COCH$_2$N($R^4$)$_2$, —N($R^6$)COCH$_2$CH$_2$N($R^4$)$_2$, and —N($R^6$)COCH$_2$CH$_2$CH$_2$N($R^4$)$_2$, wherein R is selected from hydrogen, $C_{1-6}$ aliphatic, phenyl, a 5-6 membered heteroaryl ring, or a 5-6 membered heterocyclic ring. More preferred $R^5$ substituents include —Cl, —Br, —F, —CN, —CF$_3$, —COOH, —CONHMe, —CONHEt, —NH$_2$, —NHAc, —NHSO$_2$Me, —NHSO$_2$Et, —NHSO$_2$(n-propyl), —NHSO$_2$(isopropyl), —NHCOEt, —NHCOCH$_2$NHCH$_3$, —NHCOCH$_2$N(CO$_2$t-Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO (cyclopropyl), —NHCO (isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH($C_{1-4}$ aliphatic) such as —NHMe, —N($C_{1-4}$ aliphatic)$_2$ such as —NMe$_2$, OH, —O($C_{1-4}$ aliphatic) such as —OMe, $C_{1-4}$ aliphatic such as methyl, ethyl, cyclopropyl, isopropyl, or t-butyl, and —CO$_2$($C_{1-4}$ aliphatic).

Preferred formula IIa compounds have one or more, and more preferably all, of the features selected from the group consisting of:
(a) $R^y$ is Z—$R^{3'}$ or an optionally substituted group selected from $C_{1-6}$ aliphatic, 5-6 membered heterocyclyl, phenyl, or 5-6 membered heteroaryl, wherein Z is a methylene and $R^{3'}$ is —N($R^4$)$_2$, —OR, or an optionally substituted group selected from $C_{1-6}$ aliphatic, $C_{6-10}$ aryl, a heteroaryl ring having 5-10 ring atoms, or a heterocyclyl ring having 5-10 ring atoms;
(b) $R^1$ is T-(Ring D), wherein T is a valence bond or a methylene unit;
(c) Ring D is a 5-7 membered monocyclic or an 8-10 membered bicyclic aryl or heteroaryl ring; and
(d) $R^2$ is —R or -T-W—$R^6$ and $R^{2'}$ is hydrogen, or $R^2$ and $R^{2'}$ are taken together to form an optionally substituted benzo ring.

More preferred compounds of formula IIa have one or more, and more preferably all, of the features selected from the group consisting of:
(a) $R^y$ is an optionally substituted group selected from $C_{1-6}$ aliphatic, 5-6 membered heterocyclyl, phenyl, or 5-6 membered heteroaryl;
(b) $R^1$ is T-(Ring D), wherein T is a valence bond and Q is —S—, —NH—, or —CH$_2$—;
(c) Ring D is a 5-6 membered monocyclic or an 8-10 membered bicyclic aryl or heteroaryl ring; and
(d) $R^2$ is —R and $R^{2'}$ is hydrogen, wherein R is selected from hydrogen, $C_{1-6}$ aliphatic, phenyl, a 5-6 membered heteroaryl ring, or a 5-6 membered heterocyclic ring.

Even more preferred compounds of formula IIa have one or more, and more preferably all, of the features selected from the group consisting of:
(a) $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl;
(b) $R^1$ is T-(Ring D), wherein T is a valence bond and Ring D is a 5-6 membered aryl or heteroaryl ring, wherein Ring D is optionally substituted with one to two groups selected from -halo, —CN, —NO$_2$, —N($R^4$)$_2$, optionally substituted $C_{1-6}$ aliphatic group, —OR, —CO$_2$R, —CONH($R^4$), —N($R^4$)COR, —N($R^4$)SO$_2$R, —N($R^6$)COCH$_2$N($R^4$)$_2$, or —N($R^6$)COCH$_2$CH$_2$N($R^4$)$_2$, and Q is —S— or —NH—; and
(c) $R^2$ is hydrogen or a substituted or unsubstituted $C_{1-6}$ aliphatic, and L is —O—, —S—, or —NH—.

Representative compounds of formula IIa are shown below in Table 1.
TABLE 1
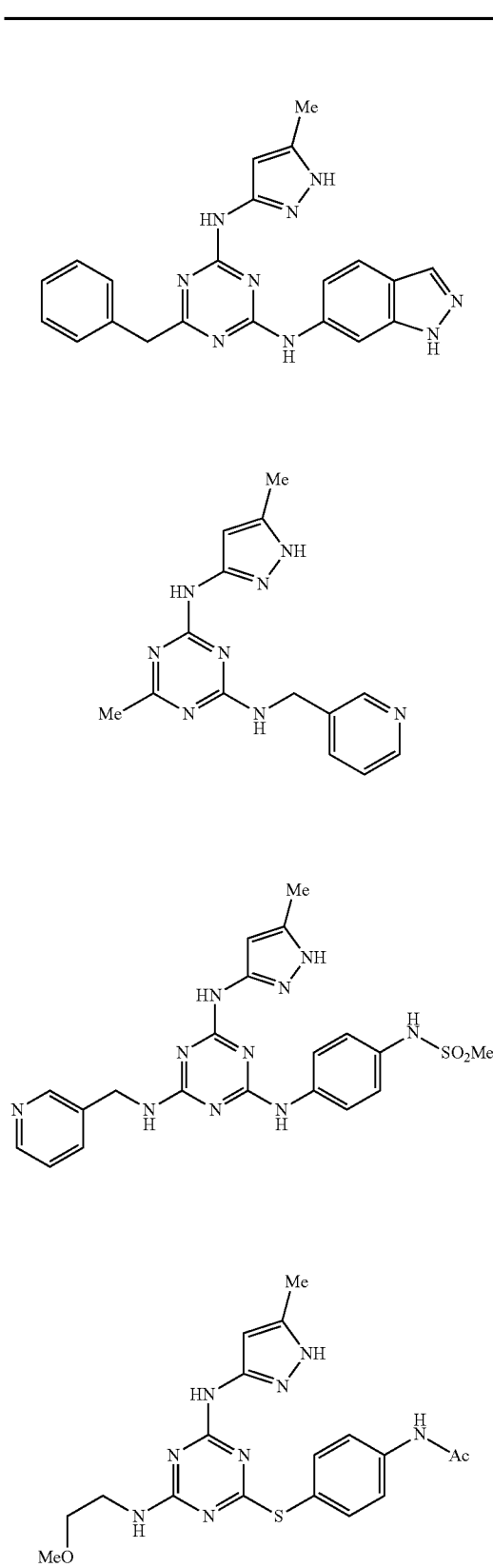
TABLE 1-continued
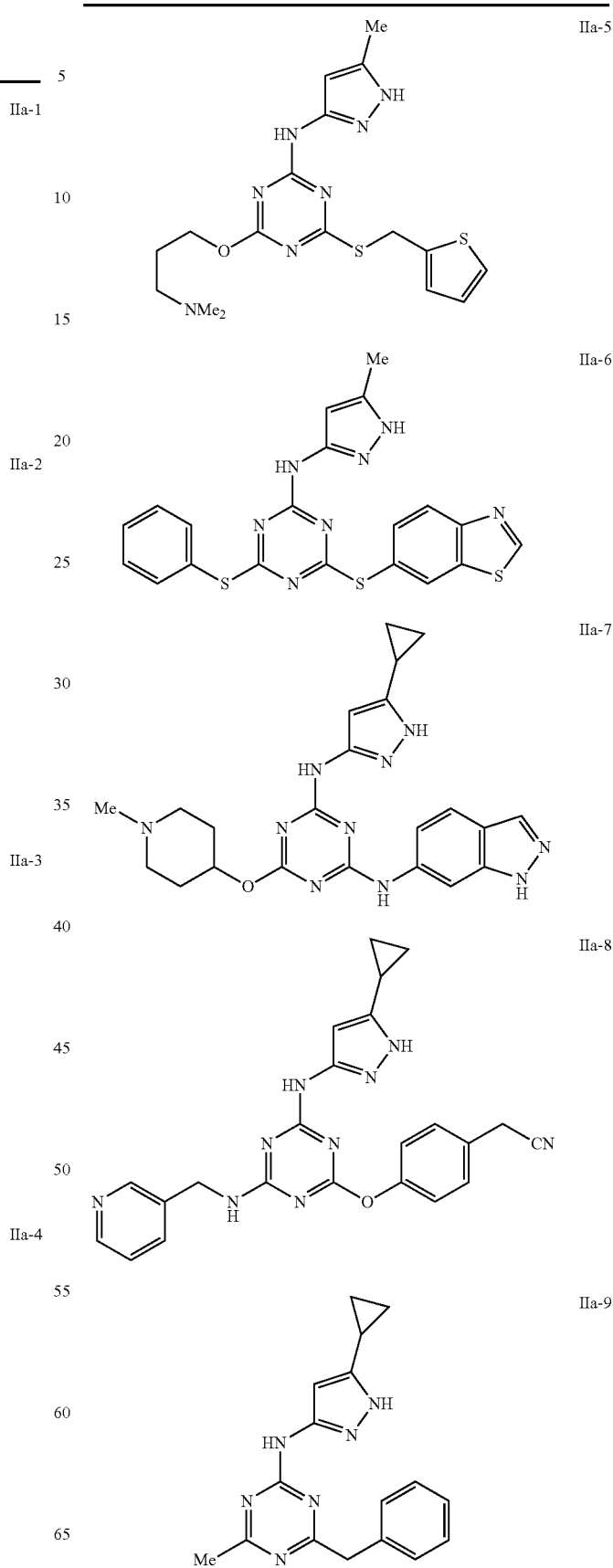

TABLE 1-continued

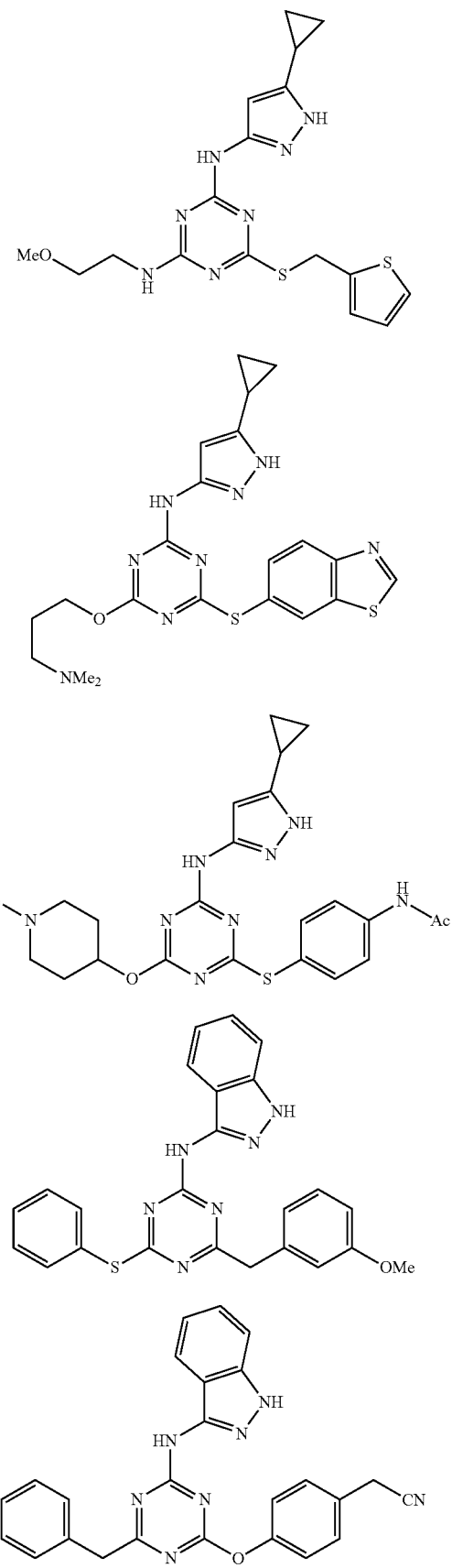

IIa-10
IIa-11
IIa-12
IIa-13
IIa-14

TABLE 1-continued

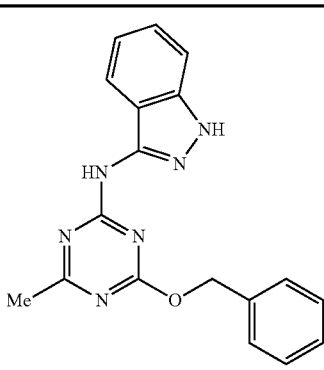

IIa-15

In another embodiment, this invention provides a composition comprising a compound of formula IIa and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIa or a pharmaceutical composition thereof.

Another aspect of this invention relates to a method of inhibiting Aurora-2 activity in a patient, which method comprises administering to the patient a compound of formula IIa or a composition comprising said compound.

Another aspect of this invention relates to a method of treating or preventing a GSK-3-mediated disease with a GSK-3 inhibitor, which method comprises administering to a patient in need of such treatment a therapeutically effective amount of a compound of formula IIa or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIa or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIa or a composition comprising said compound.

Another method relates to inhibiting Aurora-2 or GSK-3 activity in a biological sample, which method comprises contacting the biological sample with the Aurora-2 or GSK-3 inhibitor of formula IIa, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IIa, as described above.

Another embodiment of this invention relates to compounds of formula IIb:

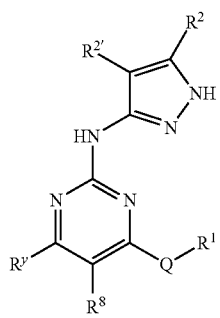

IIb or a pharmaceutically acceptable derivative or prodrug thereof, wherein:

$R^y$ is Z—$R^{3'}$ or an optionally substituted group selected from $C_{1-6}$ aliphatic, $C_{6-10}$ aryl, a heteroaryl ring having 5-10 ring atoms, or a heterocyclyl ring having 5-10 ring atoms, or $R^y$ and $R^8$ are taken together to form a fused, optionally substituted 5-7 membered, unsaturated or partially unsaturated, ring having 0-3 ring heteroatoms selected from nitrogen, oxygen, or sulfur;

Q is selected from —N($R^4$)—, —O—, —S—, or —CH($R^6$)—;

$R^1$ is T-(Ring D);

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;

T is a valence bond or a $C_{1-4}$ alkylidene chain, wherein when Q is —CH($R^6$)—, a methylene unit of said $C_{1-4}$ alkylidene chain is optionally replaced by —O—, —S—, —N($R^4$)—, —CO—, —CONH—, —NHCO—, —$SO_2$—, —$SO_2$NH—, —NH$SO_2$—, —$CO_2$—, —OC(O)—, —OC(O)NH—, or —NHCO$_2$—;

Z is a $C_{1-4}$ alkylidene chain;

L is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

$R^2$ and $R^{2'}$ are independently selected from —R, -T-W—$R^6$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by —$R^4$;

$R^{3'}$ is selected from -halo, —OR, —C(=O)R, —$CO_2$R, —COCOR, —COCH$_2$COR, —$NO_2$, —CN, —S(O)R, —S(O)$_2$R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, —OC(=O)N($R^7$)$_2$, or an optionally substituted group selected from $C_{1-6}$ aliphatic, $C_{6-10}$ aryl, a heteroaryl ring having 5-10 ring atoms, or a heterocyclyl ring having 5-10 ring atoms;

each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;

each $R^4$ is independently selected from —$R^7$, —COR$^7$, —$CO_2$ (optionally substituted $C_{1-6}$ aliphatic), —CON($R^7$)$_2$, or —$SO_2$$R^7$;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5-8 membered heterocyclyl or heteroaryl ring; and $R^8$ is selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$; provided that when Q is —NH— and $R^y$ and $R^8$ are taken together to form a fused ring, $R^1$ is other than a pyrazol-3-yl ring or a pyrazol-3-yl-containing bicyclic ring system.

Preferred $R^y$ groups of formula IIb include Z—$R^{3'}$ or an optionally substituted group selected from $C_{1-6}$ aliphatic, 5-6 membered heterocyclyl, phenyl, or 5-6 membered heteroaryl, wherein Z is a methylene and $R^{3'}$ is —N($R^4$)$_2$, —OR, or an optionally substituted group selected from $C_{1-6}$ aliphatic, $C_{6-10}$ aryl, a heteroaryl ring having 5-ring atoms, or a heterocyclyl ring having 5-10 ring atoms.

Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The $R^2$ and $R^{2'}$ groups of formula IIb may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIb compounds having a pyrazole-containing bicyclic ring system:

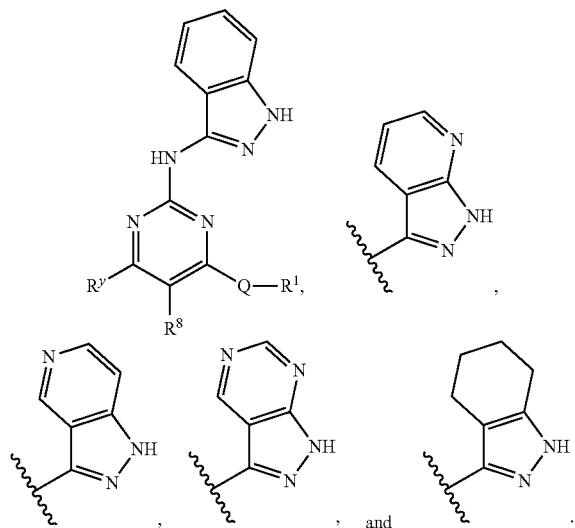

Preferred substituents on the $R^2/R^{2'}$ fused ring of formula IIb include one or more of the following: -halo, $-N(R^4)_2$, $-C_{1-4}$ alkyl, $-C_{1-4}$ haloalkyl, $-NO_2$, $-O(C_{1-4}$ alkyl), $-CO_2(C_{1-4}$ alkyl), $-CN$, $-SO_2(C_{1-4}$ alkyl), $-SO_2NH_2$, $-OC(O)NH_2$, $-NH_2SO_2(C_{1-4}$ alkyl), $-NHC(O)$ $(C_{1-4}$ alkyl), $-C(O)NH_2$, and $-CO(C_{1-4}$ alkyl), wherein the $(C_{1-4}$ alkyl) is a straight, branched, or cyclic alkyl group. Preferably, the $(C_{1-4}$ alkyl) group is methyl.

When the pyrazole ring system of formula IIb is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIb is monocyclic, preferred Ring D groups include phenyl, pyridyl, pyridazinyl, pyrimidinyl, and pyrazinyl.

When Ring D of formula IIb is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIb, preferred $T-R^5$ or $V-Z-R^5$ substituents include -halo, $-CN$, $-NO_2$, $-N(R^4)_2$, optionally substituted $C_{1-6}$ aliphatic group, $-OR$, $-C(O)R$, $-CO_2R$, $-CONH(R^4)$, $-N(R^4)COR$, $-N(R^4)CO_2R$, $-SO_2N(R^4)_2$, $-N(R^4)SO_2R$, $-N(R^6)COCH_2N(R^4)_2$, $-N(R^6)COCH_2CH_2N(R^4)_2$, and $-N(R^6)COCH_2CH_2CH_2N(R^4)_2$, wherein R is selected from hydrogen, $C_{1-6}$ aliphatic, phenyl, a 5-6 membered heteroaryl ring, or a 5-6 membered heterocyclic ring. More preferred $R^5$ substituents include $-Cl$, $-Br$, $-F$, $-CN$, $-CF_3$, $-COOH$, $-CONHMe$, $-CONHEt$, $-NH_2$, $-NHAc$, $-NHSO_2Me$, $-NHSO_2Et$, $-NHSO_2(n-propyl)$, $-NHSO_2$ (isopropyl), $-NHCOEt$, $-NHCOCH_2NHCH_3$, $-NHCOCH_2N(CO_2t-Bu)CH_3$, $-NHCOCH_2N(CH_3)_2$, $-NHCOCH_2CH_2N(CH_3)_2$, $-NHCOCH_2CH_2CH_2N(CH_3)_2$, $-NHCO(cyclopropyl)$, $-NHCO(isobutyl)$, $-NHCOCH_2(morpholin-4-yl)$, $-NHCOCH_2CH_2(morpholin-4-yl)$, $-NHCOCH_2CH_2CH_2(morpholin-4-yl)$, $-NHCO_2(t-butyl)$, $-NH(C_{1-4}$ aliphatic) such as $-NHMe$, $-N(C_{1-4}$ aliphatic)$_2$ such as $-NMe_2$, $OH$, $-O(C_{1-4}$ aliphatic) such as $-OMe$, $C_{1-4}$ aliphatic such as methyl, ethyl, cyclopropyl, isopropyl, or t-butyl, and $-CO_2(C_{1-4}$ aliphatic).

When $R^y$ and $R^8$ are taken together to form a fused ring, preferred rings formed by $R^y$ and $R^8$ include 5-6 membered unsaturated or partially unsaturated rings having 0-2 heteroatoms. More preferred fused rings formed by $R^y$ and $R^8$ include benzo, cyclohexo, and pyrido.

Preferred $R^8$ groups of formula IIb, when present, include R, OR, and $N(R^4)_2$. Examples of preferred $R^8$ include methyl, ethyl, $NH_2$, $NH_2CH_2CH_2NH$, $N(CH_3)_2CH_2CH_2NH$, $N(CH_3)_2CH_2CH_2O$, (piperidin-1-yl) $CH_2CH_2O$, and $NH_2CH_2CH_2O$.

Preferred formula IIb compounds have one or more, and more preferably all, of the features selected from the group consisting of:
(a) $R^y$ is $Z-R^{3'}$ or an optionally substituted group selected from $C_{1-6}$ aliphatic, 5-6 membered heterocyclyl, phenyl, or 5-6 membered heteroaryl, wherein Z is a methylene and $R^{3'}$ is $-N(R^4)_2$, $-OR$, or an optionally substituted group selected from $C_{1-6}$ aliphatic, $C_{6-10}$ aryl, a heteroaryl ring having 5-10 ring atoms, or a heterocyclyl ring having 5-10 ring atoms;
(b) $R^1$ is T-(Ring D), wherein T is a valence bond or a methylene unit;
(c) Ring D is a 5-7 membered monocyclic or an 8-10 membered bicyclic aryl or heteroaryl ring; and
(d) $R^2$ is $-R$ or $-T-W-R^6$ and $R^{2'}$ is hydrogen, or $R^2$ and $R^{2'}$ are taken together to form an optionally substituted benzo ring.

More preferred compounds of formula IIb have one or more, and more preferably all, of the features selected from the group consisting of:
(a) $R^y$ is an optionally substituted group selected from $C_{1-6}$ aliphatic, 5-6 membered heterocyclyl, phenyl, or 5-6 membered heteroaryl;
(b) $R^1$ is T-(Ring D), wherein T is a valence bond, and Q is $-S-$, $-NH-$, or $-CH_2-$;
(c) Ring D is a 5-6 membered monocyclic or an 8-10 membered bicyclic aryl or heteroaryl ring; and
(d) $R^2$ is $-R$ and $R^{2'}$ is hydrogen, wherein R is selected from hydrogen, $C_{1-6}$ aliphatic, phenyl, a 5-6 membered heteroaryl ring, or a 5-6 membered heterocyclic ring.

Even more preferred compounds of formula IIb have one or more, and more preferably all, of the features selected from the group consisting of:
(a) $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl, or $R^y$ and $R^8$ are taken together to form a 5-6 membered unsaturated or partially unsaturated ring having 0-2 heteroatoms selected from nitrogen, oxygen, or sulfur;

(b) R¹ is T-(Ring D), wherein T is a valence bond and Ring D is a 5-6 membered aryl or heteroaryl ring, wherein Ring D is optionally substituted with one to two groups selected from -halo, —CN, —NO₂, —N(R⁴)₂, optionally substituted C₁₋₆ aliphatic group, —OR, —CO₂R, —CONH(R⁴), —N(R⁴)COR, —N(R⁴)SO₂R, —N(R⁶)COCH₂CH₂N(R⁴)₂, or —N(R⁶)COCH₂CH₂CH₂N(R⁴)₂, and Q is —S— or —NH—; and (c) R² is hydrogen or a substituted or unsubstituted C₁₋₆ aliphatic, and L is —O—, —S—, or —NH—.

Representative compounds of formula IIb are shown below in Table 2.

TABLE 2

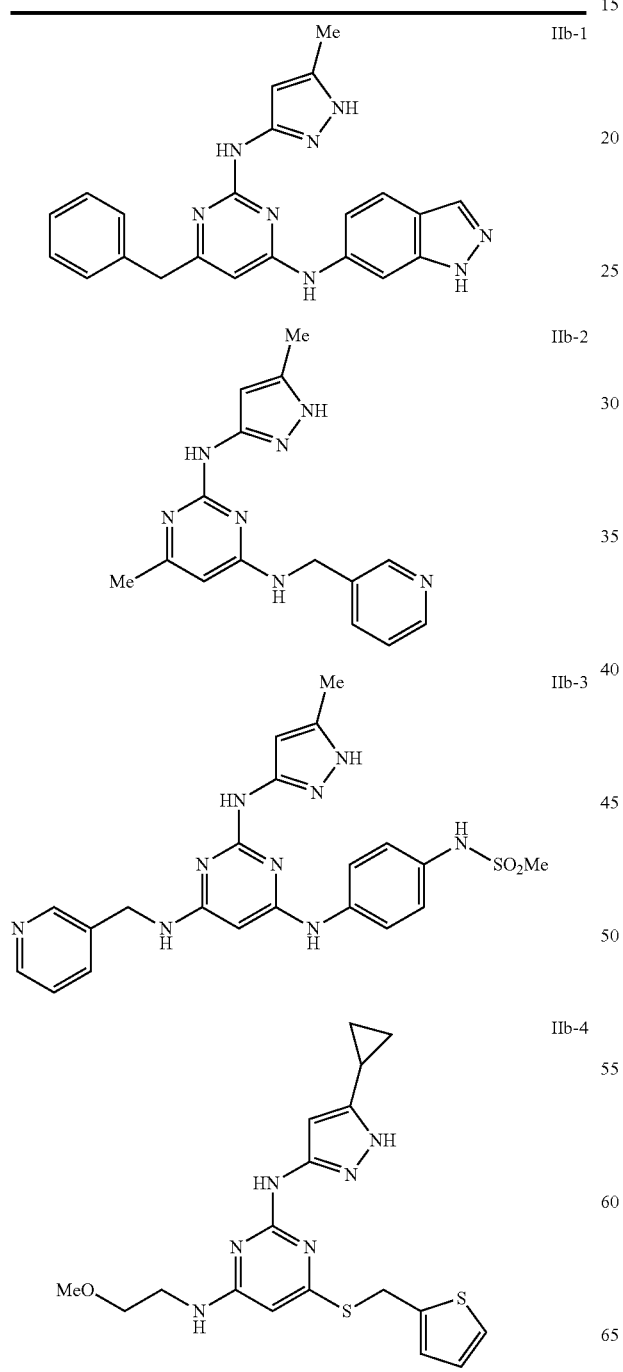

TABLE 2-continued

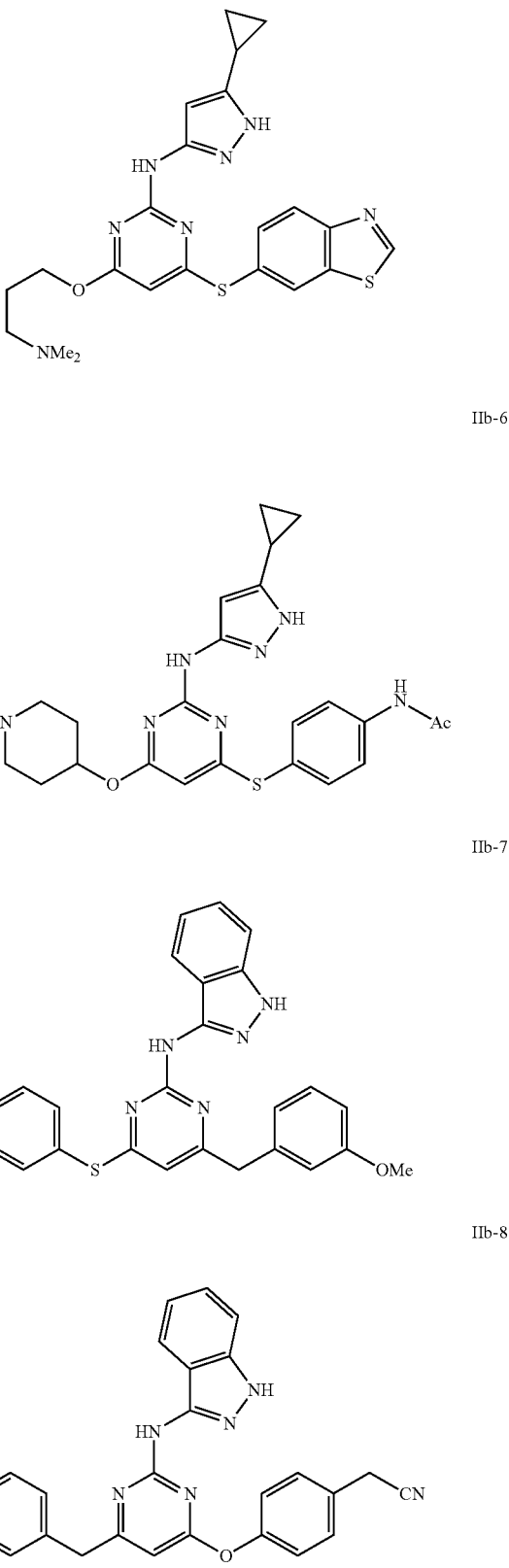

TABLE 2-continued

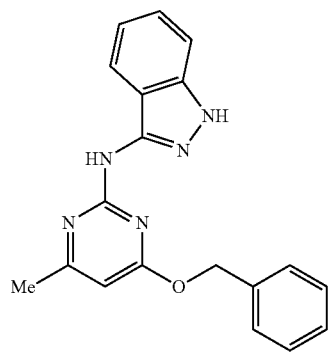 [SMILES: Cc1cc(OCc2ccccc2)nc(Nc2n[nH]c3ccccc23)n1]
IIb-9

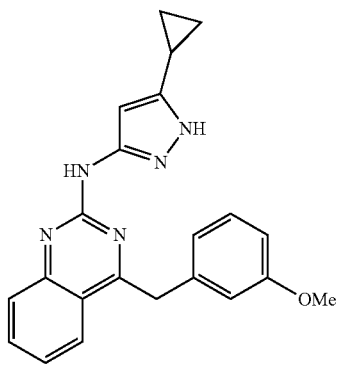
IIb-13

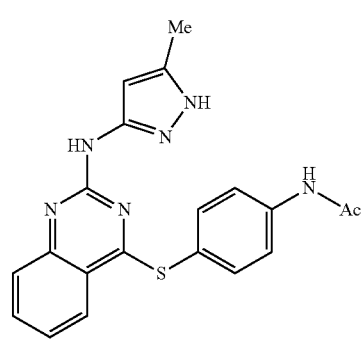 [SMILES: CC(=O)Nc1ccc(Sc2nc(Nc3cc(C)[nH]n3)nc3ccccc23)cc1]
IIb-10

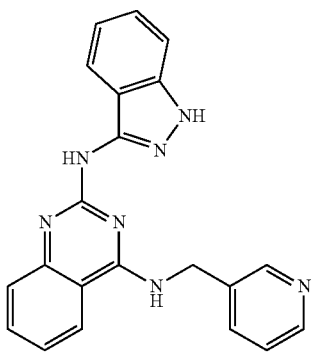
IIb-14

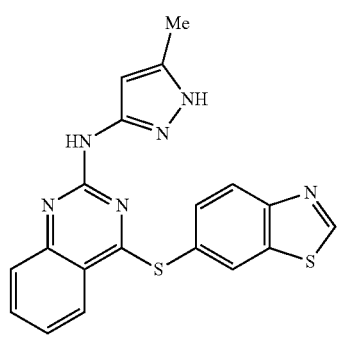 [SMILES: Cc1cc(Nc2nc(Sc3ccc4ncsc4c3)c3ccccc3n2)n[nH]1]
IIb-11

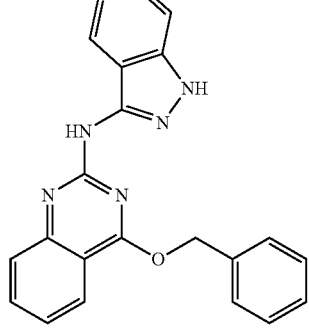
IIb-15

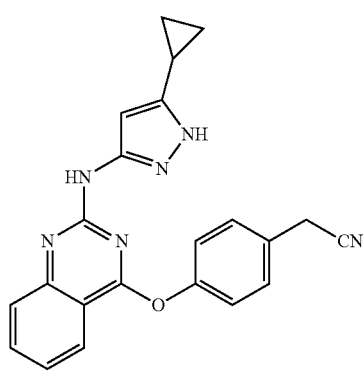 [SMILES: N#CCc1ccc(Oc2nc(Nc3cc(C4CC4)[nH]n3)nc3ccccc23)cc1]
IIb-12

In another embodiment, this invention provides a composition comprising a compound of formula IIb and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIb or a pharmaceutical composition thereof.

Another aspect of this invention relates to a method of inhibiting Aurora-2 activity in a patient, which method comprises administering to the patient a compound of formula IIb or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIb or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIb or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIb or a composition comprising said compound.

Another method relates to inhibiting Aurora-2 or GSK-3 activity in a biological sample, which method comprises contacting the biological sample with the Aurora-2 or GSK-3 inhibitor of formula IIb, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IIb, as described above.

Another embodiment of this invention relates to compounds of formula III:

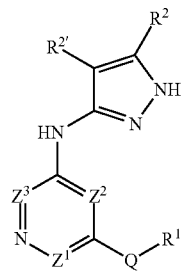

III or a pharmaceutically acceptable derivative or prodrug thereof, wherein:

$Z^1$ is nitrogen or $CR^8$, $Z^2$ is nitrogen or CH, and $Z^3$ is nitrogen or $CR^x$, provided that one of $Z^1$ and $Z^3$ is nitrogen;

$R^x$ is T-$R^3$ or L-Z-$R^3$;

Q is selected from —N($R^4$)—, —O—, —S—, or —CH($R^6$)—;

$R^1$ is T-(Ring D);

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;

T is a valence bond or a $C_{1-4}$ alkylidene chain, wherein when Q is —CH($R^6$)—, a methylene unit of said $C_{1-4}$ alkylidene chain is optionally replaced by —O—, —S—, —N($R^4$)—, —CO—, —CONH—, —NHCO—, —$SO_2$—, —$SO_2$NH—, —NHSO_2—, —$CO_2$—, —OC(O)—, —OC(O)NH—, or —NHCO_2—;

Z is a $C_{1-4}$ alkylidene chain;

L is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO_2—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

$R^2$ and $R^{2'}$ are independently selected from —R, -T-W—$R^6$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —$CO_2$R, —COCOR, —COCH_2COR, —$NO_2$, —CN, —S(O)R, —S(O)$_2$R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;

each $R^4$ is independently selected from —$R^7$, —COR^7, —$CO_2$ (optionally substituted $C_{1-6}$ aliphatic), —CON($R^7$)$_2$, or —$SO_2$$R^7$;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO_2—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$SO_2—, —C($R^6$)$_2$$SO_2$N($R^6$)—, —C($R^6$)$_2$N($R^6$)—, —CO—, —$CO_2$—, —C($R^6$) OC(O)—, —C($R^6$) OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5-8 membered heterocyclyl or heteroaryl ring; and $R^8$ is selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—

OR, —N(R⁴)CON(R⁴)₂, —N(R⁴)SO₂N(R⁴)₂, —N(R⁴)SO₂R, or —OC(=O)N(R⁴)₂.

Accordingly, the present invention relates to compounds of formula IIIa, IIIb, IIIc and IIId as shown below:

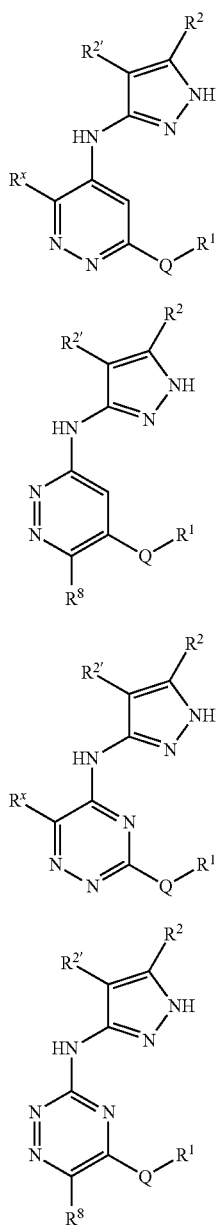

Preferred R$^x$ groups of formula III include T-R³ wherein T is a valence bond or a methylene and R³ is CN, —R, or —OR. When R³ is —R, preferred R³ groups include an optionally substituted group selected from C$_{1-6}$ aliphatic, phenyl, or a 5-6 membered heteroaryl or heterocyclyl ring. When R³ is —OR, preferred R groups include an optionally substituted group C$_{1-6}$ aliphatic group such as alkyl- or dialkylaminoalkyl and aminoalkyl. Examples of preferred R$^x$ include acetamido, CN, piperidinyl, piperazinyl, phenyl, pyridinyl, imidazol-1-yl, imidazol-2-yl, cyclohexyl, cyclopropyl, methyl, ethyl, isopropyl, t-butyl, NH₂CH₂CH₂NH, and NH₂CH₂CH₂O.

Preferred R⁸ groups of formula III, when present, include R, OR, and N(R⁴)₂. Examples of preferred R⁸ include methyl, ethyl, NH₂, NH₂CH₂CH₂NH, N(CH₃)₂CH₂CH₂NH, N(CH₃)₂CH₂CH₂O, (piperidin-1-yl) CH₂CH₂O, and NH₂CH₂CH₂O.

The R² and R$^{2'}$ groups of formula III may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula III compounds having a pyrazole-containing bicyclic ring system:

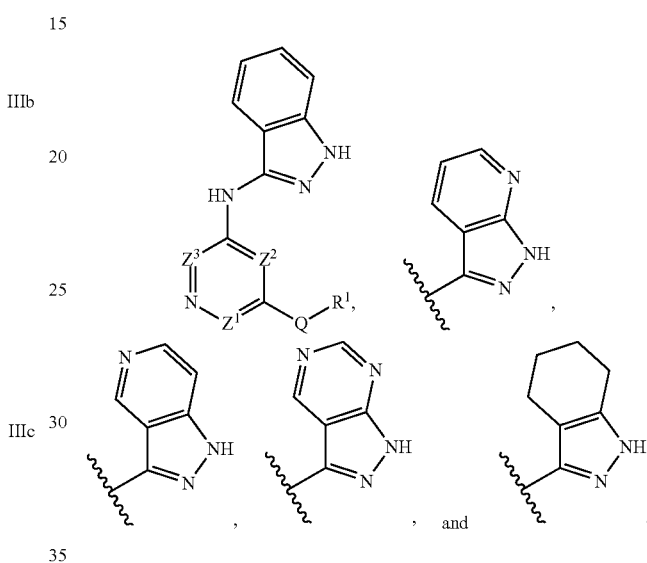

Preferred substituents on the formula III R²/R$^{2'}$ fused ring include one or more of the following: -halo, —N(R⁴)₂, —C$_{1-4}$ alkyl, —C$_{1-4}$ haloalkyl, —NO₂, —O(C$_{1-4}$ alkyl), —CO₂(C$_{1-4}$ alkyl), —CN, —SO₂(C$_{1-4}$ alkyl), —SO₂NH₂, —OC(O)NH₂, —NH₂SO₂(C$_{1-4}$ alkyl), —NHC(O)(C$_{1-4}$ alkyl), —C(O)NH₂, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula III is monocyclic, preferred R² groups include hydrogen or a substituted or unsubstituted group selected from aryl, heteroaryl, or a C$_{1-6}$ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R$^{2'}$ group is hydrogen.

When Ring D of formula III is monocyclic, preferred Ring D groups include phenyl, pyridyl, pyridazinyl, pyrimidinyl, and pyrazinyl.

When Ring D of formula III is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula III, preferred T-R⁵ or V—Z—R⁵ substituents include -halo, —CN, —NO₂, —N(R⁴)₂, optionally substituted C$_{1-6}$ aliphatic group, —OR, —C(O)R, —CO₂R, —CON(R⁴)₂, —OCO(R⁴)₂, —N(R⁴)COR, —N(R⁴)CO₂R, —SO₂N(R⁴)₂, —N(R⁴)SO₂R, —N(R⁶)

COCH$_2$N(R$^4$)$_2$, —N(R$^6$)COCH$_2$CH$_2$N(R$^4$)$_2$, and —N(R$^6$)COCH$_2$CH$_2$CH$_2$N(R$^4$)$_2$, wherein R is selected from hydrogen, C$_{1-6}$ aliphatic, phenyl, a 5-6 membered heteroaryl ring, or a 5-6 membered heterocyclic ring. More preferred R$^5$ substituents include —Cl, —Br, —F, —CN, —CF$_3$, —COOH, —CONHMe, —CONHEt, —NH$_2$, —NHAc, —NHSO$_2$Me, —NHSO$_2$Et, —NHSO$_2$(n-propyl), —NHSO$_2$(isopropyl), —NHCOEt, —NHCOCH$_2$NHCH$_3$, —NHCOCH$_2$N(CO$_2$t-Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO(cyclopropyl), —NHCO(isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH(C$_{1-4}$ aliphatic) such as —NHMe, —N(C$_{1-4}$ aliphatic)$_2$ such as —NMe$_2$, OH, —O(C$_{1-4}$ aliphatic) such as —OMe, C$_{1-4}$ aliphatic such as methyl, ethyl, cyclopropyl, isopropyl, or t-butyl, and —CO$_2$(C$_{1-4}$ aliphatic).

Preferred compounds of formula IIIa, IIIb, IIIc, or IIId have one or more, and more preferably all, of the features selected from the group consisting of:

(a) R$^x$ is hydrogen, alkyl- or dialkylamino, acetamido, or a C$_{1-4}$ aliphatic group;

(b) R$^1$ is T-(Ring D), wherein T is a valence bond or a methylene unit;

(c) Ring D is a 5-7 membered monocyclic or an 8-10 membered bicyclic aryl or heteroaryl ring; and (d) R$^2$ is —R or -T-W—R$^6$ and R$^{2'}$ is hydrogen, or R$^2$ and R$^{2'}$ are taken together to form an optionally substituted benzo ring.

More preferred compounds of formula IIIa, IIIb, IIIc, or IIId have one or more, and more preferably all, of the features selected from the group consisting of:

(a) R$^1$ is T-(Ring D), wherein T is a valence bond, and Q is —S—, —NH—, or —CH$_2$—;

(b) Ring D is a 5-6 membered monocyclic or an 8-10 membered bicyclic aryl or heteroaryl ring; and (c) R$^2$ is —R and R$^{2'}$ is hydrogen, wherein R is selected from hydrogen, C$_{1-6}$ aliphatic, phenyl, a 5-6 membered heteroaryl ring, or a 5-6 membered heterocyclic ring.

Even more preferred compounds of formula IIIa, IIIb, IIIc, or IIId have one or more, and more preferably all, of the features selected from the group consisting of:

(a) R$^x$ is hydrogen methyl, ethyl, propyl, cyclopropyl, isopropyl, methylamino or acetimido;

(b) R$^1$ is T-(Ring D), wherein T is a valence bond and Ring D is a 5-6 membered aryl or heteroaryl ring, wherein Ring D is optionally substituted with one to two groups selected from -halo, —CN, —NO$_2$, —N(R$^4$)$_2$, optionally substituted C$_{1-6}$ aliphatic group, —OR, —CO$_2$R, —CON(R$^4$)$_2$, —OCO(R$^4$)$_2$, —N(R$^4$)COR, —N(R$^4$)SO$_2$R, —N(R$^6$)COCH$_2$CH$_2$N(R$^4$)$_2$, or —N(R$^6$)COCH$_2$CH$_2$CH$_2$N(R$^4$)$_2$, and Q is —S— or —NH—; and (c) R$^2$ is hydrogen or a substituted or unsubstituted C$_{1-6}$ aliphatic.

Representative compounds of formula III are shown below in Table 3.

TABLE 3

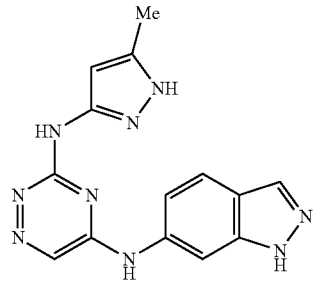 [SMILES: Cc1cc(Nc2nncc(Nc3ccc4cn[nH]c4c3)n2)n[nH]1]

III-1

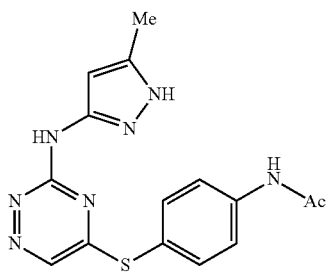 [SMILES: CC(=O)Nc1ccc(Sc2cnnc(Nc3cc(C)[nH]n3)n2)cc1]

III-2

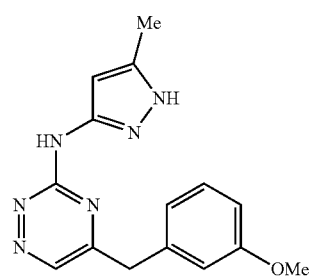 [SMILES: COc1cccc(Cc2cnnc(Nc3cc(C)[nH]n3)n2)c1]

III-3

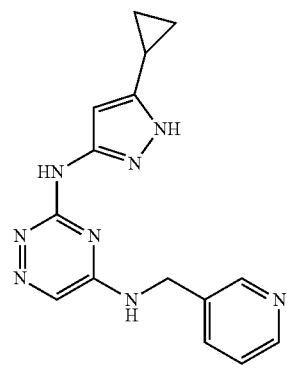 [SMILES: c1cncc(CNc2cnnc(Nc3cc(C4CC4)[nH]n3)n2)c1]

III-4

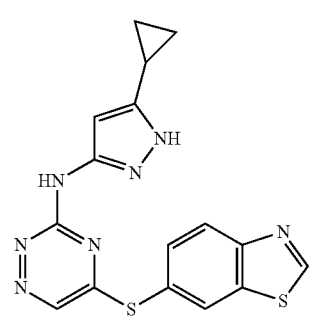 [SMILES: c1nc2ccc(Sc3cnnc(Nc4cc(C5CC5)[nH]n4)n3)cc2s1]

III-5

TABLE 3-continued
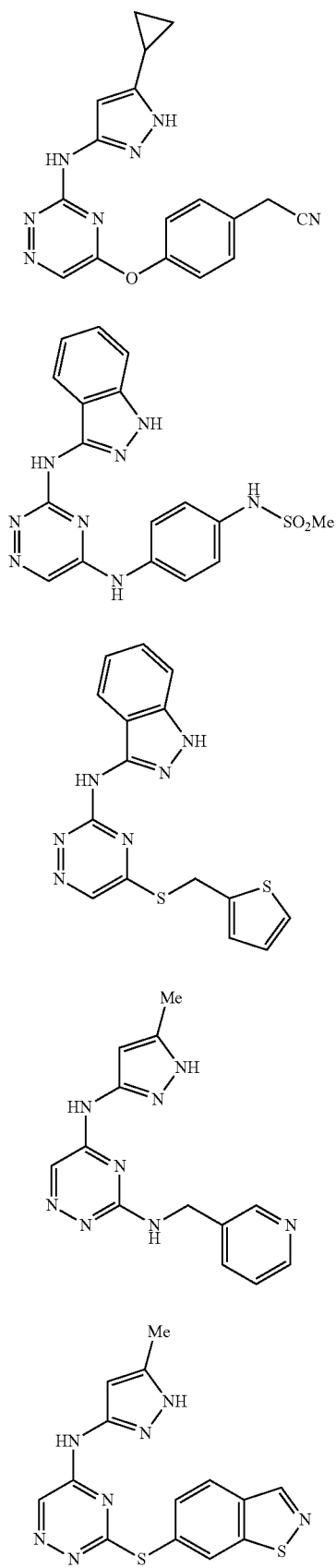
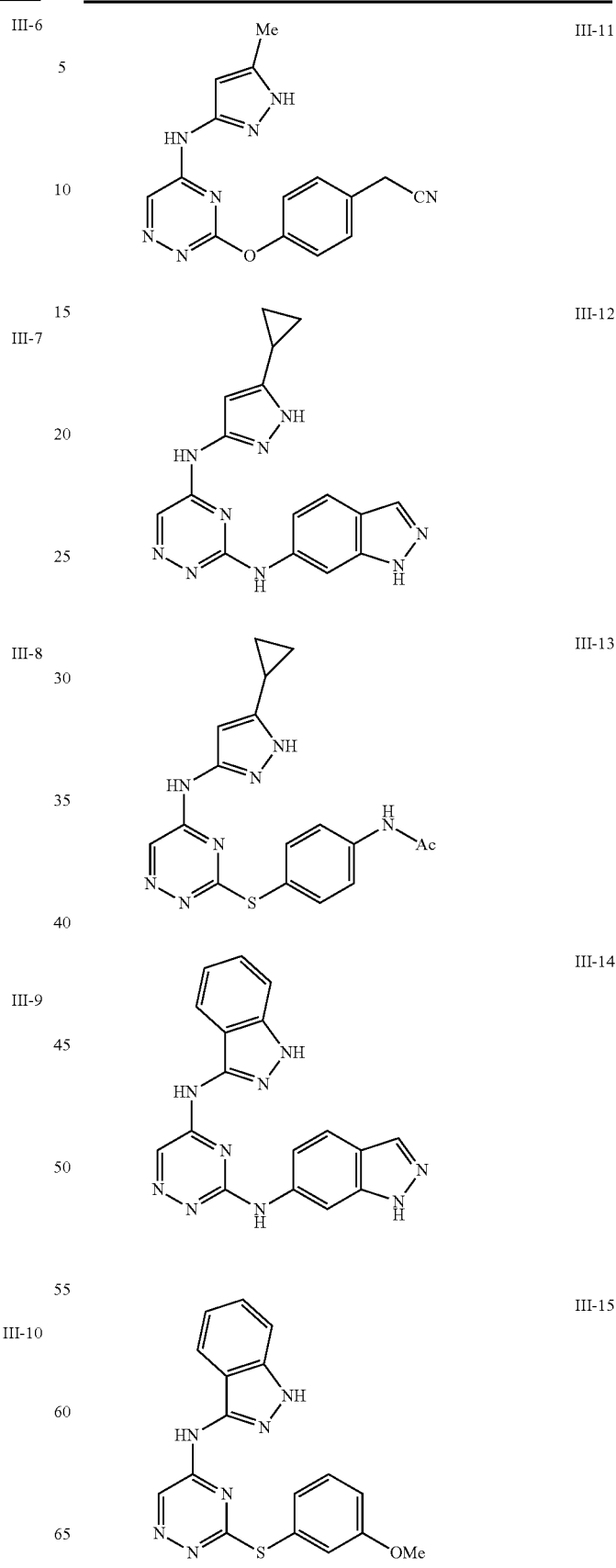

TABLE 3-continued
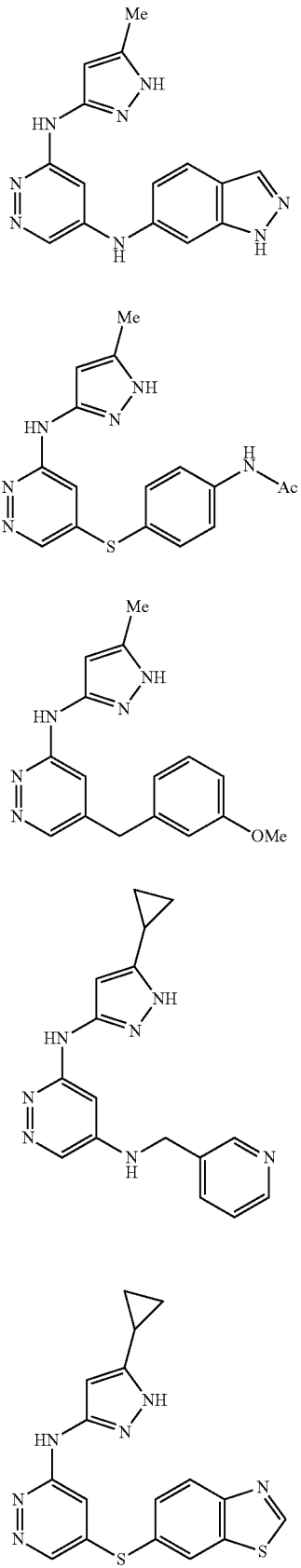
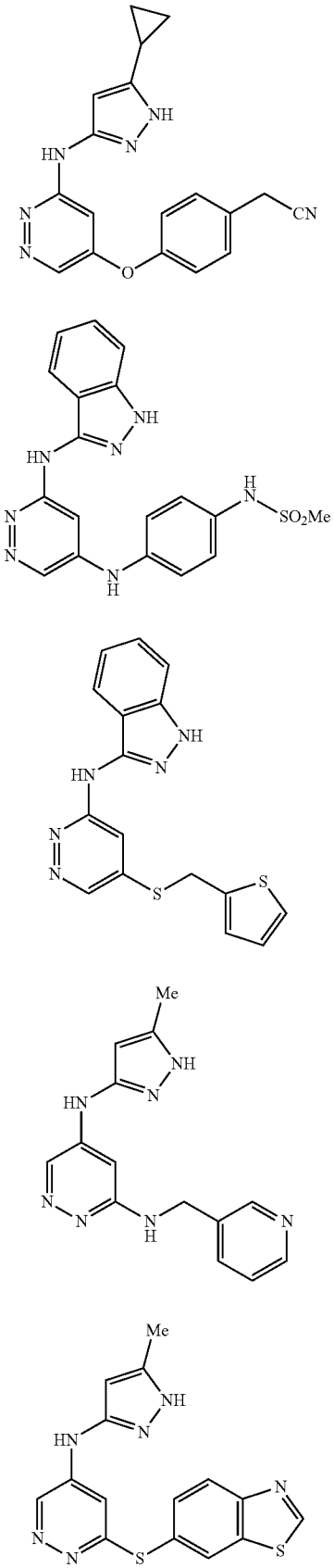

TABLE 3-continued

| | |
|---|---|
| 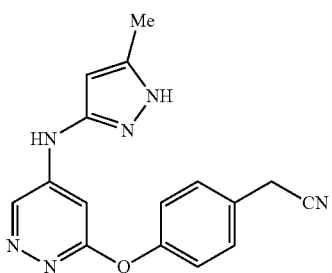 [SMILES: Cc1cc(Nc2cnnc(Oc3ccc(CC#N)cc3)c2)n[nH]1] | III-26 |
| 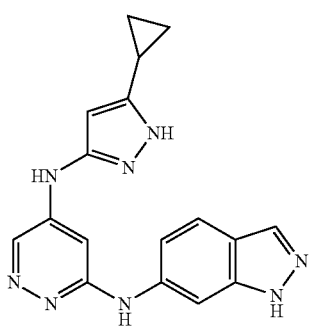 [SMILES: c1cc2cn[nH]c2cc1Nc1cc(Nc2cc(C3CC3)[nH]n2)cnn1] | III-27 |
| 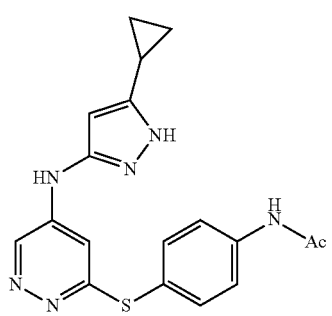 [SMILES: CC(=O)Nc1ccc(Sc2cc(Nc3cc(C4CC4)[nH]n3)cnn2)cc1] | III-28 |
| 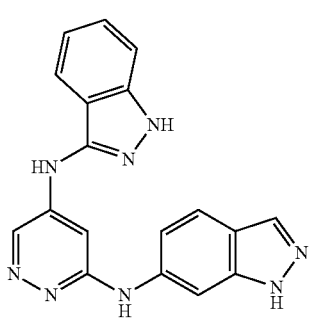 [SMILES: c1ccc2c(Nc3cnnc(Nc4ccc5cn[nH]c5c4)c3)n[nH]c2c1] | III-29 |
| 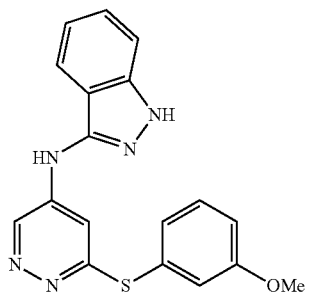 [SMILES: COc1cccc(Sc2cc(Nc3n[nH]c4ccccc34)cnn2)c1] | III-30 |

In another embodiment, this invention provides a composition comprising a compound of formula III and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula III or a pharmaceutical composition thereof.

Another aspect of this invention relates to a method of inhibiting Aurora-2 activity in a patient, which method comprises administering to the patient a compound of formula III or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula III or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula III or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula III or a composition comprising said compound.

Another method relates to inhibiting Aurora-2 or GSK-3 activity in a biological sample, which method comprises contacting the biological sample with the Aurora-2 or GSK-3 inhibitor of formula III, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula III as described above.

The compounds of this invention may be prepared in general by methods known to those skilled in the art for analogous compounds, as illustrated by the general Schemes I-VII.

Scheme I

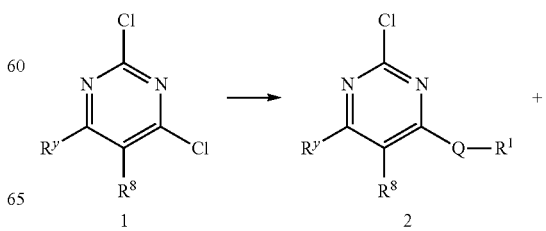

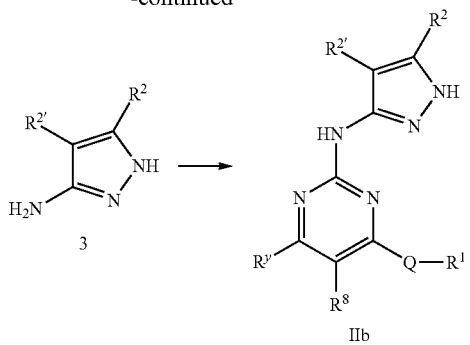

Scheme I above shows a general route for the preparation of compounds of formula IIb. The dichloro intermediate 1 (prepared using methods similar to those reported in *J. Indian. Chem. Soc.*, 61, 690-693 (1984) or in *J. Med. Chem.*, 37, 3828-3833 (1994)) is sequentially reacted with two nucleophiles: $R^1$-QH to displace the chloride at position 4 to afford intermediate 2; and then 2 is treated with an aminopyrazole (or aminoindazole) to displace the chloride at position 2, using procedures similar to those described in *J. Med. Chem*, 38, 14, 2763-2773, (1995) to afford compounds of formula IIb.

Scheme II above shows a general route for the preparation of compounds of formula IIb wherein Q is an N, O or S linker and $R^y$ is a group attached to the pyrimidine core via a heteroatom. Starting material 4,6-dihydroxy-2-methylsulfanylpyrimidine (4) is prepared using procedures similar to those reported in *J. Med. Chem.*, 27, 12, 1621-1629 (1984). Chlorination of 4 with $POCl_3$ affords the dichloro intermediate 5. The two chlorides of 5 are sequentially displaced with the appropriate $R^1$-QH, to afford compound 6, and then with $R^y$—H (amine, alcohol, or thiol) to afford compound 7 using procedures similar to those reported in U.S. Pat. No. 2,585,906. Alternatively, the order of displacement may be reversed by first displacing with $R^y$—H and then with $R^1$-QH. The methyl sulfanyl group of compound 7 is then oxidized (for example, with oxone) to afford compound 8 and the resulting methylsulfonyl is finally displaced with the amino moiety of aminopyrazole (or aminoindazole) by methods substantially similar to those described above for Scheme 1 step (b) to afford compounds of formula IIb.

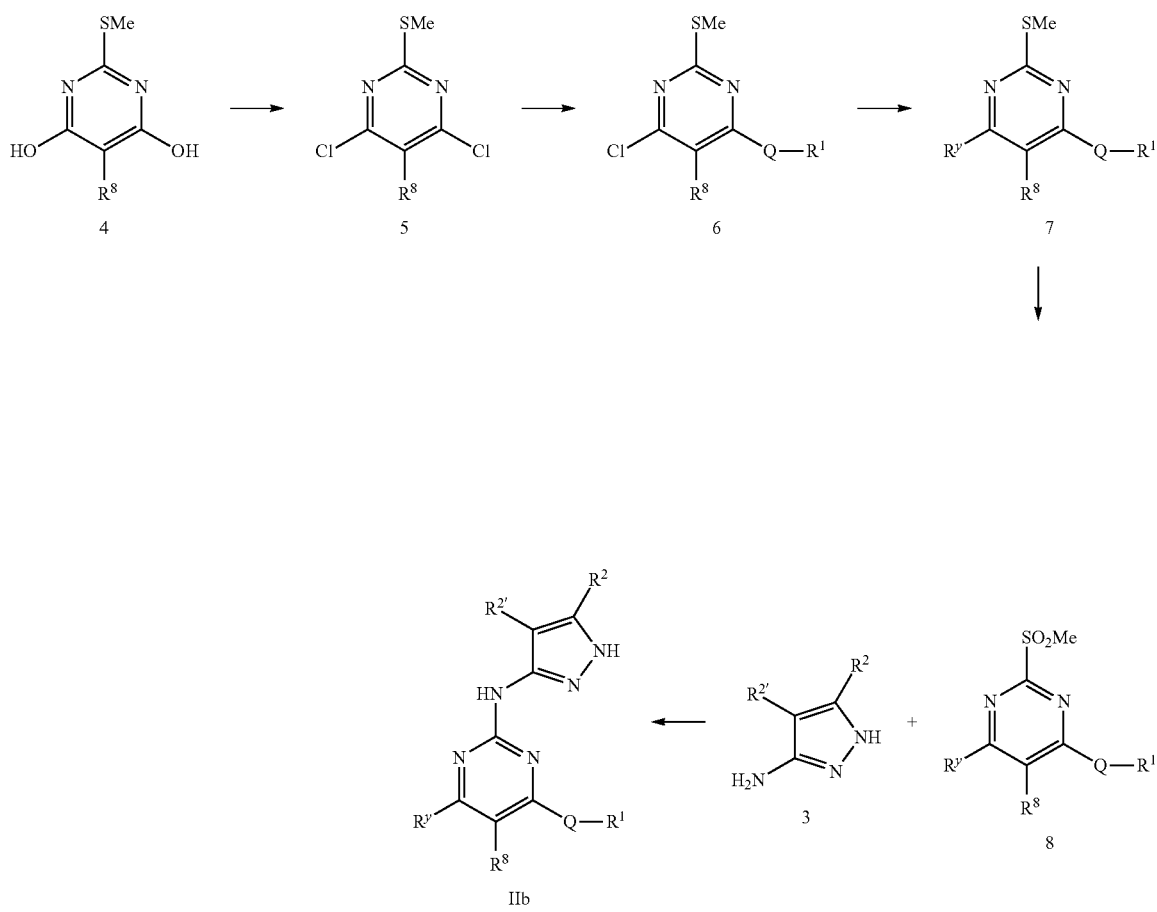

Scheme III

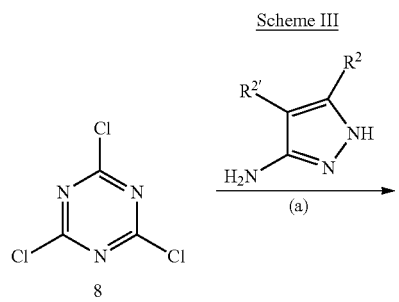

Scheme IV

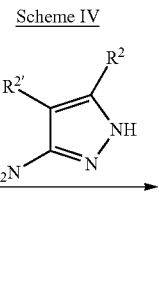

Scheme III above shows a general route for the preparation of compounds of formula IIa. The three chlorides of starting material 8 are sequentially displaced with (a) the amino moiety of aminopyrazole (or aminoindazole) to afford compound 9, (b) the $R^1$-QH group to afford compound 10, and (c) $R^y$—H (amine, alcohol, or thiol) using procedures similar to the ones reported in *J. Indian Chem. Soc.*, 53, 207-208, (1976) to afford compounds of formula IIa. These three steps can also be performed in different order to afford compounds of formula IIa.

Scheme IV above shows a general route for the preparation of compounds of formula IIIa. Treatment of 11 with aminopyrazole (or aminoindazole) to provide 12 may be performed in a manner similar to that described in *Heterocycles,* 51, 5, 1999, 1035-1050. The intermediate 13 is obtained by displacement with $R^1$-QH in a manner similar to that described in *Farmaco. Ed. Sci.*, 27, 1972, 591-600. For the preparation of compounds of formula IIIa where $R^x$ is hydrogen, the chlorine may be removed by reduction. Alternatively, for the preparation of compounds of formula IIIa where $R^x$ is other than hydrogen, the chlorine may be displaced by methods known to those skilled in the art to afford compounds with a variety of $R^x$ substituents.

Scheme V

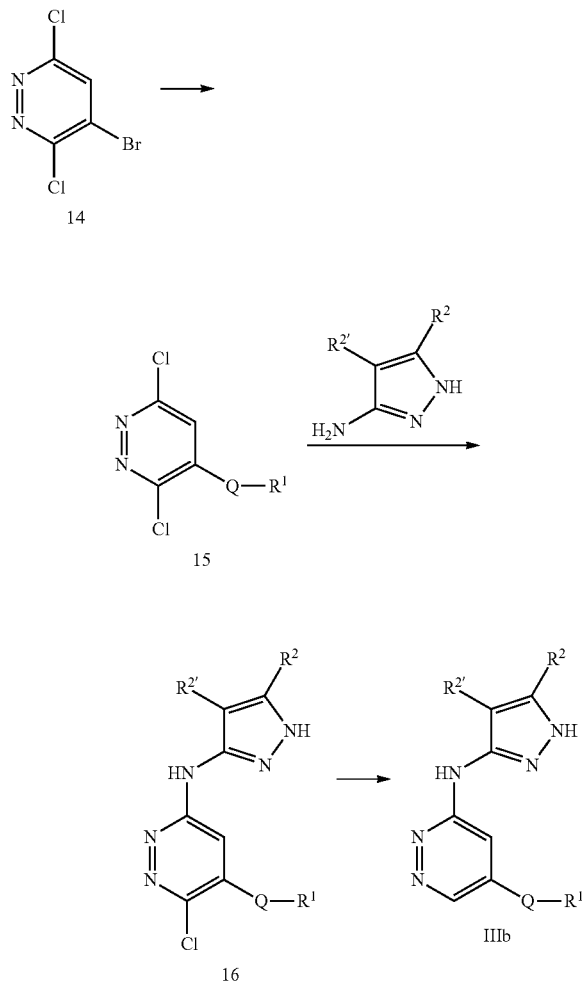

Scheme V above shows a general route for the preparation of the compounds of formula IIIb. Displacement of the bromide with R¹-QH to afford compound may be performed in a manner similar to that described in *Heterocycles*, 51, 5, 1999, 1035-1050. Displacement of the chlorines may be carried out sequentially as described above.

Scheme VI

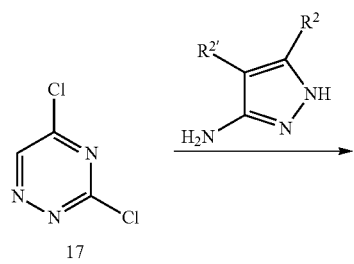

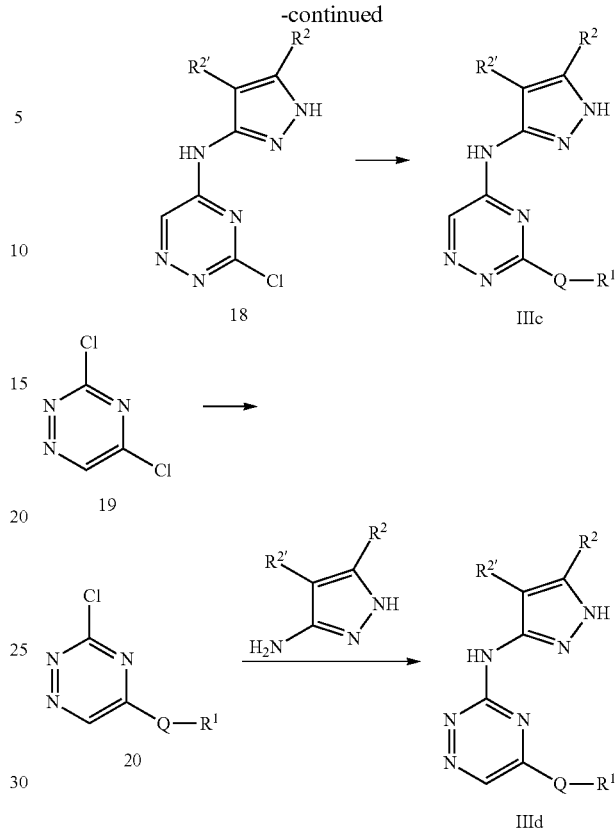

Scheme VI above shows a general route for the preparation of the compounds of formulae IIIc and IIId. The displacement with aminopyrazole (or aminoindazole) followed by the displacement with R¹-QH may be performed in a manner similar to that described in *Indian J. Chem. Sect. B,* 29, 5, 1990, 435-439.

In order that the invention described herein may be more fully understood, the following examples are set forth. It should be understood that these examples are for illustrative purposes only and are not to be construed as limiting this invention in any manner.

Biological Testing

The activity of the compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

BIOLOGICAL TESTING EXAMPLE 1

$K_i$ Determination for the Inhibition of GSK-3

Compounds are screened for their ability to inhibit GSK-3β (AA 1-420) activity using a standard coupled enzyme system (Fox et al. (1998) *Protein Sci.* 7, 2249). Reactions are carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay are 20 μM ATP (Sigma Chemicals, St Louis, Mo.) and 300 μM peptide (HSSPHQS(PO$_3$H$_2$)EDEEE, American Peptide, Sunnyvale, Calif.).

Reactions are carried out at 30° C. and 20 nM GSK-3β. Final concentrations of the components of the coupled enzyme system are 2.5 mM phosphoenolpyruvate, 300 μM NADH, 30 μg/ml pyruvate kinase and 10 μg/ml lactate dehydrogenase.

An assay stock buffer solution is prepared containing all of the reagents listed above with the exception of ATP and the test compound of interest. The assay stock buffer solution (175 μl) is incubated in a 96 well plate with 5 μl of the test compound of interest at final concentrations spanning 0.002 μM to 30 μM at 30° C. for 10 min. Typically, a 12 point titration is conducted by preparing serial dilutions (from 10 mM compound stocks) with DMSO of the test compounds in daughter plates. The reaction is initiated by the addition of 20 μl of ATP (final concentration 20 μM). Rates of reaction are obtained using a Molecular Devices Spectramax plate reader (Sunnyvale, Calif.) over 10 min at 30° C. The K$_i$ values are determined from the rate data as a function of inhibitor concentration.

BIOLOGICAL TESTING EXAMPLE 2

K$_i$ Determination for the Inhibition of Aurora-2

Compounds are screened in the following manner for their ability to inhibit Aurora-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) is added a DMSO solution of a compound of the present invention to a final concentration of 30 μM. The resulting mixture is incubated at 30° C. for 10 min. The reaction is initiated by the addition of 10 μL of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The K$_i$ values are determined from the rate data as a function of inhibitor concentration.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula III:

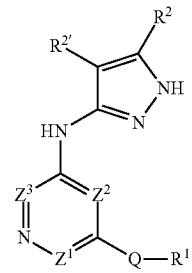

or a pharmaceutically acceptable salt thereof; wherein:
$Z^1$ is CH;
$Z^2$ is CH or N;
$Z^3$ is N;
Q is NH, O, —CH($R^6$)—, or S;
$R^1$ is T-(Ring D);
Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;
T is a valence bond or a $C_{1-4}$ alkylidene chain;
Z is a $C_{1-4}$ alkylidene chain;
$R^2$ and $R^{2'}$ are independently selected from $C^{1-4}$ alkyl, a 3-6 membered cycloalkyl, or $R^2$ and $R^{2'}$ are taken together with their intervening atoms to form a fused phenyl ring, wherein each substitutable ring carbon of said fused ring formed by $R^2$ and $R^{2'}$ is independently substituted by halo, oxo, —CN, —NO$_2$, —$R^7$, or —V—$R^6$;
each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;
each $R^4$ is independently selected from —$R^7$, —COR$^7$, —CO$_2$(optionally substituted $C_{1-6}$ aliphatic), —CON($R^7$)$_2$, or —SO$_2R^7$;
each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;
V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;
each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5-8 membered heterocyclyl or heteroaryl ring.

2. The compound of claim 1, wherein Q is S.

3. The compound of claim 1, wherein Q is NH.

4. The compound of any one of claims 1-3, wherein $Z^2$ is CH.

5. The compound of any one of claims 1-3, wherein $Z^2$ is N.

6. The compound of claim 5, wherein $R^1$ is phenyl, pyridyl, indazolyl, benzothiazolyl, or thiophene.

7. The compound of claim 6, wherein $R^1$ is phenyl.

8. The compound of claim 5, wherein $R^1$ is thiophene or phenyl.

9. The compound of claim 1, selected from:

III-1

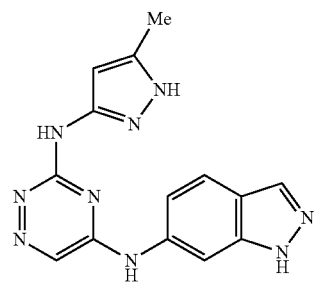

III-2

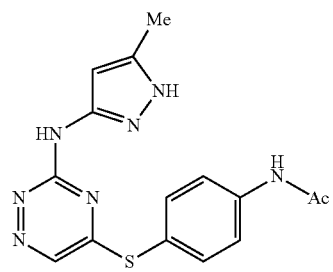

III-3

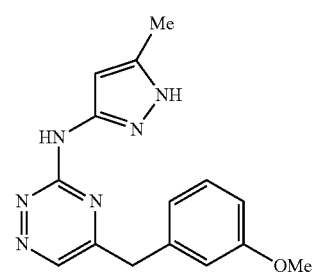

-continued

III-4

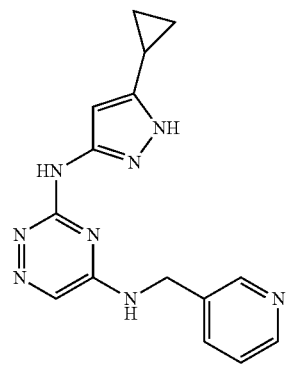

III-5

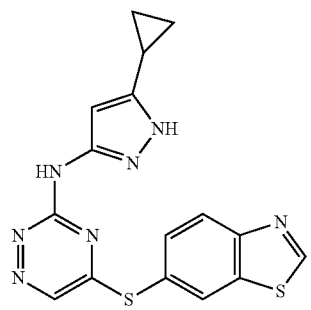

III-6

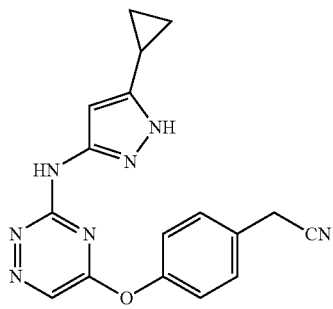

III-7

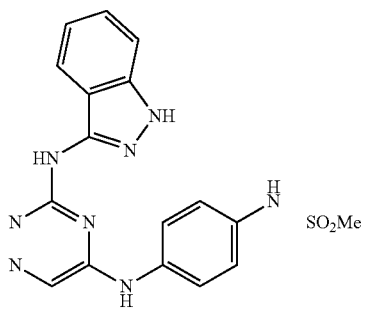

III-8

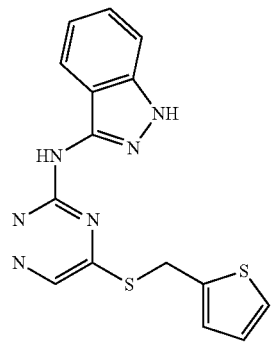

III-16
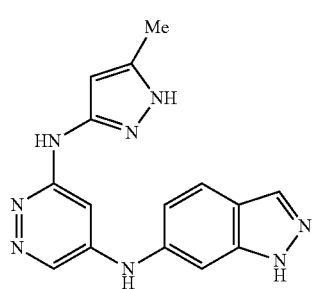
III-17
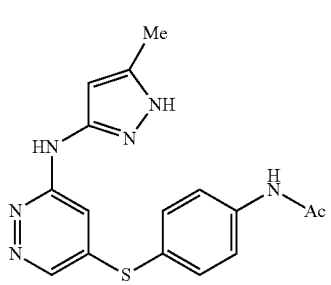
III-18
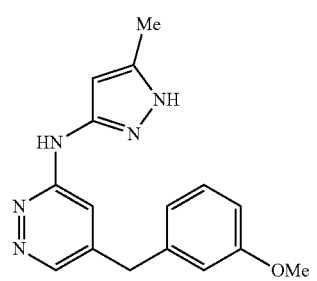
III-19
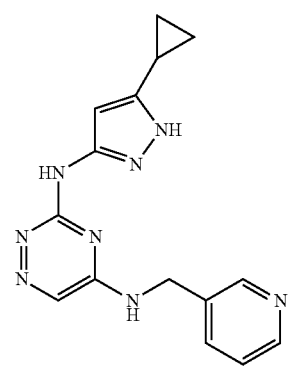
III-20
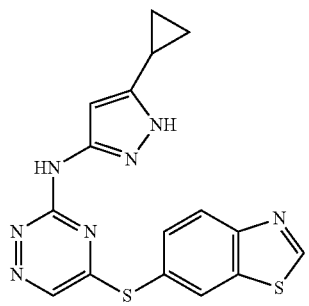
III-21
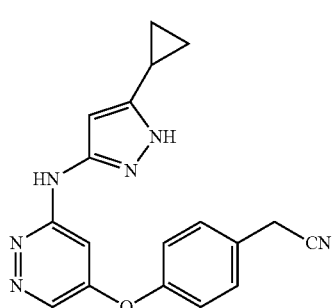
III-22
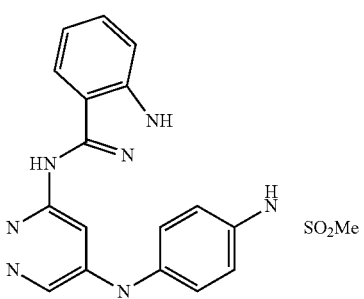
III-23
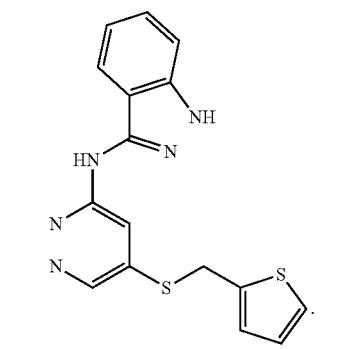
10. A composition comprising a compound according to any of claims 1 or 9, and a pharmaceutically acceptable carrier.
* * * * *